US006541231B1

United States Patent
Baszczynski et al.

(10) Patent No.: US 6,541,231 B1
(45) Date of Patent: Apr. 1, 2003

(54) METHOD FOR THE INTEGRATION OF FOREIGN DNA INTO EUKARYOTIC GENOMES

(75) Inventors: Christopher L. Baszczynski, Urbandale, IA (US); Leszek Alexander Lyznik, Johnston, IA (US); William J. Gordon-Kamm, Urbandale, IA (US); Xueni Guan, San Diego, CA (US); Aragula Gururaj Rao, Urbandale, IA (US); Laura A. Tagliani, Ankeny, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/415,839

(22) Filed: Oct. 12, 1999

Related U.S. Application Data

(62) Division of application No. 09/193,503, filed on Nov. 17, 1998.
(60) Provisional application No. 60/099,435, filed on Sep. 8, 1998, provisional application No. 60/065,627, filed on Nov. 18, 1997, and provisional application No. 60/065,613, filed on Nov. 18, 1997.

(51) Int. Cl.$^7$ .............................. C12N 9/00; C12N 9/10; C12N 15/82; C12P 21/06; C12P 21/04
(52) U.S. Cl. ...................... 435/183; 435/193; 435/69.1; 435/69.7; 435/462; 435/468; 800/278
(58) Field of Search ................................. 438/69.1, 462, 438/468, 69.7, 69.9, 419, 183, 193; 800/278

(56) References Cited

U.S. PATENT DOCUMENTS

| | | | |
|---|---|---|---|
| 5,677,177 A | | 10/1997 | Wahl et al. |
| 5,744,336 A | * | 4/1998 | Hodges et al. |
| 6,010,884 A | | 1/2000 | Griffiths et al. |
| 6,171,861 B1 | | 1/2001 | Hartley et al. |
| 6,187,994 B1 | | 2/2001 | Baszczynski et al. |
| 6,300,545 B1 | | 10/2001 | Baszczynski et al. |
| 6,331,661 B1 | | 12/2001 | Baszczynski et al. |

FOREIGN PATENT DOCUMENTS

| | | | |
|---|---|---|---|
| WO | WO 92/15694 | | 9/1992 |
| WO | WO 93/01283 | | 1/1993 |
| WO | WO 94/17176 | | 8/1994 |
| WO | WO 95/00555 | | 1/1995 |
| WO | WO-95/00555 | * | 1/1995 |
| WO | WO 96/04393 | | 2/1996 |
| WO | WO 97/09436 | | 3/1997 |
| WO | WO 97/09439 | | 3/1997 |
| WO | WO 97/13401 | | 4/1997 |
| WO | WO 97/37012 | | 10/1997 |
| WO | WO 97/47758 | | 12/1997 |
| WO | WO 99/23202 | | 5/1999 |
| WO | WO 99/55851 | | 11/1999 |

OTHER PUBLICATIONS

Dildine et al., A chimeric Ty3/moloney murine leukemia virus integrase protein is active in vivo, 1998, Journal of Virology, pp. 4297–4307.*
Narasimhulu et al., Early Transcription of Agrobacterium T–DNA Genes in Tobacco and Maize, The Plant Cell, May 1996, pp. 873–886, vol. 8, American Society of Plant Physiologists.
Osborne, B., et al., "A System for Insertional Mutagenesis and Chromosomal Rearrangement Using the Ds Transposon and Cre–lox," 1995, *The Plant Journal*, pp. 687–701, vol. 7(4).
Araki et al. (1997) "Targeted Integration of DNA Using Mutant lox Sites in Embryonic Stem Cells", *Nucleic Acids Research* 25(4):868–872.
Russell et al. (1992) "Directed Excision of a Transgene From the Plant Genome", *Mol. Genet. Genet.* 234:49–59.
Storici et al. (1997) "Molecular Engineering with the FRT Sequence of the Yeast 2 μm Plasmid: [cir°] Segregant Enrichment by Counterselection for 2 μm Site–Specific Recombination", *Gene* 195:245–255.
Karreman et al. (1996) "On the Use of Double FLP Recognition Targets (FRTs) in the LTR of Retroviruses for the Construction of High Producer Cell Lines", *Nucleic Acids Research* 24(9):1616–1624.
Seibler et al. (1997) "Double–Reciprocal Crossover Mediated by FLP–Recombinase: A Concept and an Assay", *Biochemistry* 36:1740–1747.
Sauer (1992) "Identification of Cryptic lox Sites in the yeast Genome by Selection for Cre–mediated Chromosome Translocations that Confer Multiple Drug Resistance", *J. Mol. Biol.* 223:911–928.
Senecoff et al. (1988) "DNA Recognition by the FLP Recombinase of the Yeast 2μ Plasmid", *J. Mol. Biol.* 201:406–421.

(List continued on next page.)

*Primary Examiner*—Remy Yucel
*Assistant Examiner*—Konstantina Katcheves
(74) *Attorney, Agent, or Firm*—Alston & Bird LLP

(57) ABSTRACT

Compositions and methods for introducing a DNA of interest into a genomic target site are provided. In particular, the methods and compositions involve the use of a combination of target sites for two site specific recombinases and expression of a chimeric recombinase with dual target site specificity. Thus, the compositions comprise novel site-specific recombinases with specificities to multiple target sites, and nucleotide sequences and expression cassettes encoding these recombinases or target sites. The methods involve transforming a eukaryotic cell having target sites for the novel recombinase with a DNA of interest that is flanked by corresponding target sites. Expression of the recombinase results in integration of the DNA of interest into the genome of the cell. The compositions and methods of the invention have use in the construction of stably transformed eukaryotic cells, and in particular, plant cells. The methods result in the efficient targeted genomic integration of DNA by site-specific recombination.

15 Claims, 3 Drawing Sheets

OTHER PUBLICATIONS

Senecoff et al. Directionality in FLP Protein–promoted Site–Specific Recombination Is Mediated by DNA–DNA Pairing J. Biol. Chem. (Jun. 5, 1986) pp. 7380–7386 vol. 261(16) American Society of Biological Chemists, Madison, Wisconsin.

McLeod et al. Identification of the Crossover Site during FLP–Mediated Recombination in the *Saccharomyces cerevisiae* Plasmid 2 μm Circle Mol. Cell. Biol (Oct. 1986) pp. 3357–3367 vol. 6(10) American Society for Microbiology, Princeton, NJ.

Campbell et al., Codon Usage in Higher Plants, Green Algae, and Cyanobacteria, Plant Physiol., 1990, pp. 1–11, vol. 92, Houghton, Michigan.

O'Gorman et al. Recombinase–Mediated Gene Activation and Site–Specific Integration in Mammalian Cells Science (Mar. 15, 1991) pp. 1351–1355 vol. 251 Gene Expression Laboratory, The Salk Institute for Biological Studies, La Jolla, CA.

Dale et al. Gene Transfer with Subsequent Removal of the Selection Gene from the Host Genome Proc. Natl. Acad. Sci USA (Dec. 1991) pp. 10558–10562 vol. 88 Plant Gene Expression Center, US Dept. of Agriculture/Ag. Res. Svs. Albany, CA.

Russell et al. Directed Excision of a Transgene from the Plant Genome Mol Genet Genet (1992) pp. 49–59 vol. 234 Central Res. And Dev. And Agric. Prod. du Pont Experimental Station, Wilmington, DE.

Lyznik et al. Activity of Yeast FLP Recombinase in Maize and Rice Protoplasts Nucleic Acids Research (1993) pp. 969–975 vol. 21(4) Oxford University Press.

Lyznik et al., Activity of Yeast FLP Recombinase in Maize and Rice Protoplasts, Nucleic Acids Research, 1993, pp. 969–975, vol. 21, No. 4, Oxford University Press.

Schlake et al. Use of Mutated FLP Recognition Target (FRT) Sites for the Exchange of Expression Cassettes at Defined Chromosomal Loci Biochemistry (1994) pp. 12746–12751 vol. 33(43) The American Chemical Society.

Schlake and Bode, Use of Mutated FLP Recognition Target (FRT) Sites for the Exchange of Expression Cassettes at Defined Chromosomal Loci, Biochemistry, 1994, pp. 12746–12751, vol. 33, American Chemical Society.

Albert et al., Site–Specific Integration of DNA into Wildtype and Mutant Lox Sites Placed in the Plant Genome, The Plant Journal, 1995, pp. 649–655, vol. 7(4).

Ow and Medberry, Genome Manipulation Through Site–Specific Recombination, Critical Reviews in Plant Sciences, 1995, pp. 239–261, vol. 14(3), CRC Press, Inc.

Snaith et al., Multiple Cloning Sites Carrying loxP and FRT Recognition Sites for the Cre and Flp Site–Specific Recombinases, Gene, 1995, pp. 173–174, vol. 166, Elsevier Science.

Umlauf et al. The Functional Significance of DNA Sequence Structure in a Site–Specific Genetic Recombinatin Reaction pp. 1845–1852 IRL Press Limited, Oxford, England.

Lyznik et al. Heat–inducible Expression of FLP Gene in Maize Cells The Plant Journal (1995) pp. 177–186 vol. 8(2) Dept. of Botany and Plant Pathology, Purdue Univ. West Lafayette, IN.

Kilby et al. FLP Recombinase in Transgenic Plants: Constitutive Activity in Stably Transformed Tobacco and Generation of Marked Cell Clones in Arabidopsis The Plant Journal (1995) pp. 637–652 vol. 8(5) Institute of Biotech., Univ. of Cambridge, Cambridge, UK.

Albert et al. Site–Specific Integration of DNA into Wild––type and Mutant Lox Sites Placed in the Plant Genome The Plant Journal (1995) pp. 649–659 vol. 7(4) Plant Gene Expression Center, USDA/ARS–UC Berkeley, Albany, CA.

Logie et al. Ligand–Regulated Site–Specific Recombination Proc. Natl. Acad. Sci. USA (Jun. 1995) pp. 5940–5944 vol. 92 Gene Expression Program, Eur. Mol. Biol. Lab., Heidelberg, Germany.

Zhang et al. Inducible Site–Directed Recombination in Mouse Embryonic Stem Cells Nucleic Acids Research (1996) pp. 543–548 vol. 24(4) Oxford University Press.

Lyznik et al. FLP–Mediated Recombination of FRT Sites in the Maize Genome Nucleic Acids Research (1996) pp. 3784–3789 vol. 24(19) Oxford University Press.

Araki et al. Targeted Integration of DNA Using Mutant Lox sites in Embryonic Stem Cells Nucleic Acids Research (1997) pp. 868–872 vol. 25(4) Oxford University Press.

Bethke et al. Segmental Genomic Replacement by Cre–mediated Recombination: Genotoxic Stress Activation of the p53 Promoter in Single–copy Transformants Nucleic Acids Research (1997) pp. 2828–2834 vol. 25(14) National Insitutes of Health, National Institute of Diabetes, Gigestive and Kidney Disease, Bethesda, MD.

Golic et al. FLP Mediated DNA Mobilization to Specific Target Sites in Drosophila Chromosomes (1997) pp. 3665–3671 vol. 25(18) Oxford University Press.

O'Gorman et al. Protamine–Cre Recombinase Transgenes Efficiently Recombine Target Sequences in the Male Germ Line of Mice, but Not in Embryonic Stem Cells Proc. Natl. Acad. Sci. USA (Dec. 1997) pp. 14602–14607 vol. 94 Gene Expression Laboratory, The Salk Institute for Biological Studies, San Diego, CA.

Feil et al. Regulation of Cre Recombinase Activity by Mutated Estrogen Receptor Ligand–Binding Domains Biochem. and BioPhy. Res. Comm. (1997) pp. 752–757 vol. 237 Academic Press.

U.S. patent application Ser. No. 09/193,475, Baszczynski et al., filed Nov. 17, 1998.

U.S. patent application Ser. No. 09/411,826, Baszczynski et al., filed Oct. 01, 1999.

U.S. patent application Ser. No. 09/193,484, Baszczynski et al., filed Nov. 17, 1998.

U.S. patent application Ser. No. 09/193,502, Baszczynski et al., filed Nov. 17, 1998.

U.S. patent application Ser. No. 09/455,051, Baszczynski et al., filed Dec. 06, 1999.

U.S. patent application Ser. No. 09/438,239, Baszczynski et al., filed Nov. 12, 1999.

U.S. patent application Ser. No. 09/455,050, Baszczynski et al., filed Dec. 06, 1999.

U.S. patent application Ser. No. 09/439,042, Baszczynski et al., filed Nov. 12, 1999.

U.S. patent application Ser. No. 09/438,874, Baszczynski et al., filed Nov. 12, 1999.

U.S. patent application Ser. No. 09/439,158, Baszczynski et al., filed Nov. 12, 1999.

Snaith et al., Multiple Cloning Sites Carrying *loxP* and *FRT* Recognition Sites for the Cre and Flp Site–Specific Recombinases, Gene, 1995, pp. 173–174, vol. 166.

Ow et al., Genome Manipulation Through Site–Specific Recombination, Critical Reviews in Plant Sciences, (1995), pp. 239–261, vol. 14(3).

* cited by examiner

US 6,541,231 B1

METHOD FOR THE INTEGRATION OF FOREIGN DNA INTO EUKARYOTIC GENOMES

CROSS-REFERENCE TO RELATED APPLICATION

This application claims the benefit of U.S Provisional Application Ser. No. 60/099,435, filed Sep. 8, 1998, U.S. Provisional Application Ser. No. 60/065,627, filed Nov. 18, 1997, U.S. Provisional Application Ser. No. 60/065,613, filed Nov. 18, 1997, and U.S. application Ser. No. 09/193,503 filed Nov. 17, 1998 for which this application will be a divisional of, all of which are herein incorporated by reference.

FIELD OF THE INVENTION

The invention relates to the genetic modification of chromosomes. In particular, methods and compositions for the integration of DNA into a eukaryotic genome are provided.

BACKGROUND OF THE INVENTION

Several approaches have been used to integrate a DNA of interest into the genome of a plant. In the simplest method, DNA is introduced into a cell and randomly integrates into the genome through illegitimate recombination. One drawback to this method is that positional effects due to random integration make gene expression difficult to analyze.

As an alternative to illegitimate recombination, integration may be targeted to a particular site on the genome through the use of homologous recombination or site-specific recombination. In plants, where homologous recombination technology has not been developed, site-specific recombination is used to integrate a sequence of interest into an integration site that has been previously inserted into the plant host genome. If site-specific integration occurs by a single cross-over event between a chromosome and a circular extrachromosomal replicon, the entire replicon will be inserted into the chromosome. When insertion of the entire replicon is undesirable, a fragment of the replicon comprising the DNA of interest, flanked by target sites for a site-specific recombinase, may be introduced by a double reciprocal cross-over event, into a chromosome having an integration site corresponding to the target sites which flank the DNA of interest. In either case, integration is inefficient because it is reversible, that is, the integrated DNA may be excised by subsequent site-specific recombination between the target sites flanking the integrated DNA.

Several approaches have been taken to avoid excision of an integrated DNA. In one approach, expression of a site-specific recombinase, such as Cre or FLP, is temporally regulated. See O'Gorman et al. (1991) *Science* 251:1351–1355; Logie and Stewart (1995) *Proc. Natl. Acad. Sci.* 92:5940–5944; Zhang et al. (1996) *Nuc. Acid Res.* 24:543–548, Nichols et al. (1997) *Mol. Endocinol.* 11:950–961; and Feil et al. (1997) *Biochem. Biophy. Res. Comm.* 237:752–757; the contents of which are incorporated by reference. In these methods, the recombinase is briefly expressed, either transiently or inducibly, in order to allow integration. However, excision of the integrated DNA may occur before active recombinase disappears from the cell. Furthermore, intramolecular excision is kinetically favored over bi-molecular integration. Therefore, integrated DNA is inherently unstable in the presence of recombinase.

A second approach reduces excision of integrated DNA by using pairs of singly mutated target sites on both the chromosome and flanking the DNA of interest. See Albert et al. (1995) *Plant J.* 7:649–659; Schlake and Bode (1994) *Biochemistry* 33:12746–12751; O'Gorman et al. (1997) *Proc. Natl. Acad. Sci.* 94:14602–14607; and Araki et al. (1997) *Nuc. Acid Res.* 25:868–872; the contents of which are incorporated herein by reference. Recombination between singly mutated target sites results in doubly mutated target sites flanking the DNA inserted into the chromosome. The doubly mutated target sites are not well recognized by the recombinase. Thus, the inserted DNA is excised from the chromosome by a reverse reaction only at low levels. This system, however, has the disadvantage that the singly mutated target sites often do not act as efficient recombination substrates and thus the frequency of integration is reduced. In addition, transformants are unstable because excision may still occur, although at reduced frequency.

Accordingly, it is an object of the invention to provide efficient methods for site-specific integration of DNA into eukaryotic genomes which avoid subsequent excision reactions and other non-productive recombination reactions.

SUMMARY OF THE INVENTION

Compositions and methods for introducing a DNA of interest into a genomic integration site are provided. In particular, the methods and compositions involve the use of a combination of target sites for two distinctive site-specific recombinases, such as Cre and FLP, and expression of a chimeric recombinase with dual target site specificity. Thus, the compositions comprise novel site-specific recombinases with specificities to multiple target sites, and nucleotide sequences and expression cassettes encoding these recombinases or target sites. The methods involve transforming a eukaryotic cell having target sites for the novel recombinase with a DNA of interest that is flanked by corresponding target sites. Expression of either the novel chimeric recombinase or two site-specific recombinases in the eukaryotic cell results in integration of the DNA of interest into the genome. The compositions and methods of the invention have use in the construction of stably transformed eukaryotic cells, and in particular, plant cells. The methods result in the efficient targeted genomic integration of DNA by site-specific recombination.

DETAILED DESCRIPTION OF THE INVENTION

Figure 1:
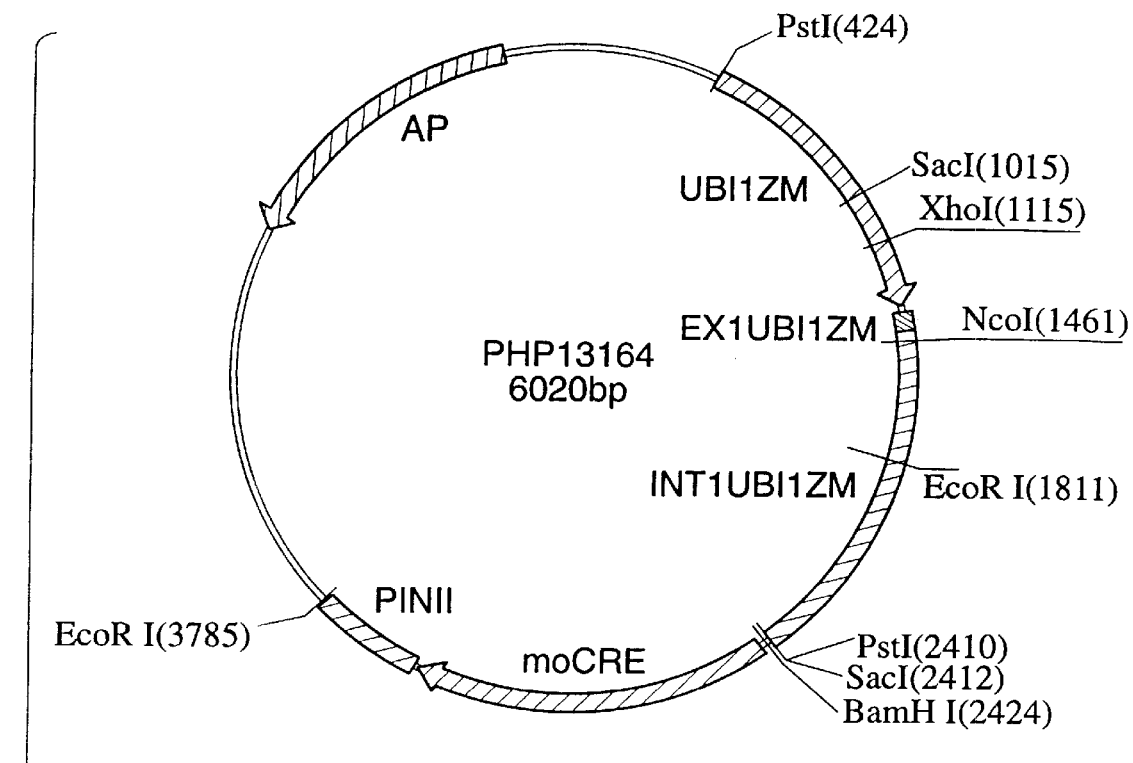
FIG. 1 schematically represents plant transformation vectors, PHP13164 and PHP13147, for expression of moCRE recombinase and Cre:FLPm recombinase, respectively.
Figure 1:
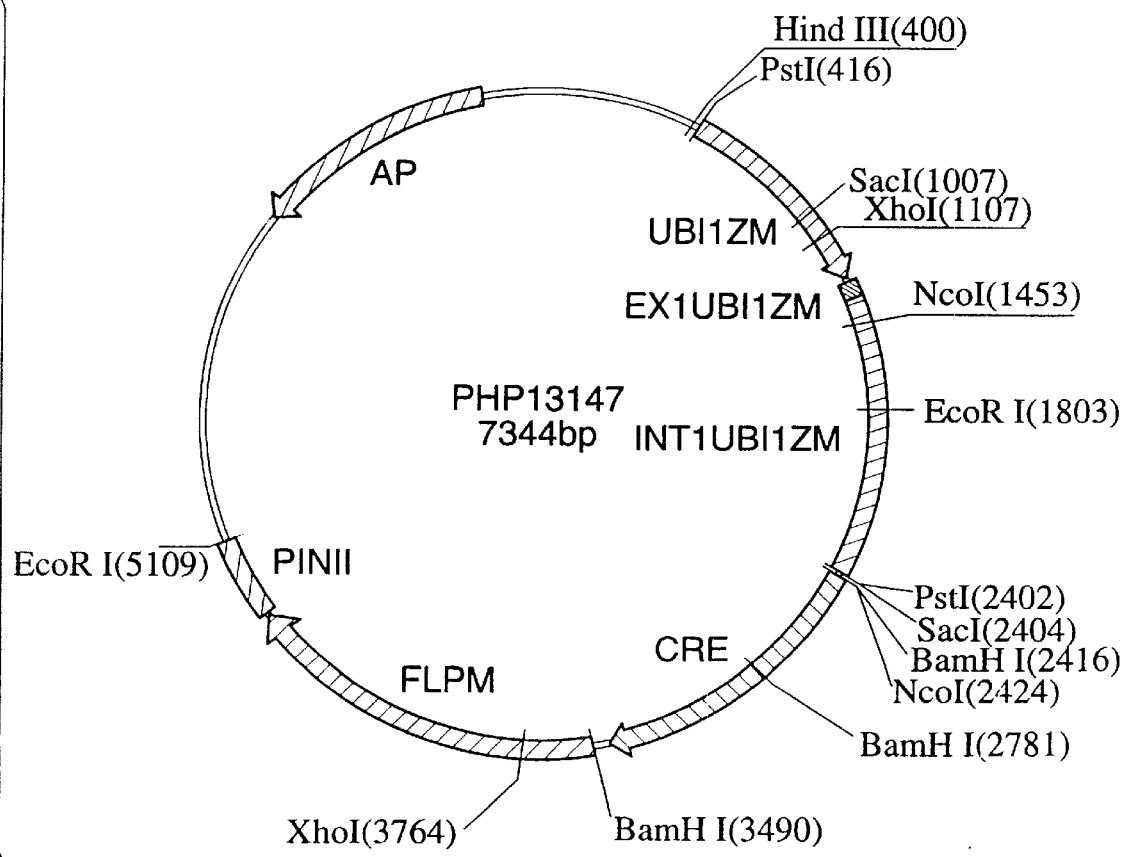

Compositions and methods for site-specific integration of DNA into predetermined genomic integration sites in a host genome are provided. The invention provides for the use of chimeric recombinases that catalyze site-specific recombination between target sites that originate from different site-specific recombination systems. Such a dual function chimeric recombinase ensures that the two ends of foreign DNA do not ligate with each other, but instead, recombine with their cognate partner target sites residing in the genomic DNA. The methods facilitate the directional targeting of desired genes and nucleotide sequences into corresponding integration sites previously introduced into the genome.

In the methods of the invention, a combination of target sites for two site-specific recombinases are introduced into the genome of an organism of interest, establishing an integration site for insertion of nucleotide sequences of interest. For the purposes of the invention, an integration site will comprise flanking target sites where the target sites correspond to the recombination sites for two distinctive site-specific recombinases. These recombination or target sites may flank other nucleotide sequences or may be contiguous. Methods for the production of transgenic plants containing specific recombination sites integrated in the plant genome are described in co-pending provisional application, serial No. 60/065,627, entitled Compositions and Methods for Genetic Modification of Plants, filed Nov. 18, 1997, and herein incorporated by reference. Once a stable plant or cultured tissue is established, a transfer cassette comprising a DNA of interest, flanked by target sites corresponding to those of the genomic integration site, is introduced into the stably transformed plant or tissues in the presence of a chimeric recombinase with specificities to each of the target sites. Alternatively, two distinct recombinases corresponding to the target sites may be present in the cell in lieu of a chimeric recombinase. This process results in exchange of the nucleotide sequences between the two identical target sites of the genomic integration site and the transfer cassette.

Thus, the invention provides a method for integrating a DNA of interest into the genome of a eukaryotic cell, comprising:
  a) transforming said cell with a transfer cassette comprising said DNA, wherein said DNA is flanked by a target site for a first site-specific recombinase and a target site for a second site-specific recombinase, and said genome contains an integration site comprising target sites corresponding to said target sites flanking said DNA, and
  b) providing in said cell a recombinant protein comprising said first recombinase fused in frame with said second recombinase.

The invention further provides a method for integrating a DNA of interest into the genome of a eukaryotic cell, comprising:
  a) transforming said cell with a transfer cassette comprising said DNA, wherein said DNA is flanked by a target site for a first site-specific recombinase and a target site for a second site-specific recombinase, and said genome contains an integration site comprising target sites corresponding to said target sites flanking said DNA; and
  b) providing in said cell said first recombinase and said second recombinase.

By "site-specific recombinase" is meant any enzyme that catalyzes conservative site-specific recombination between its corresponding recombination sites. For reviews of site-specific recombinases, see Sauer (1994) *Current Opinion in Biotechnology* 5:521–527, and Sadowski (1993) *FASEB* 7:760–767, the contents of which are incorporated herein by reference.

The first and second site-specific recombinases may be full length recombinases and/or active fragments or derivatives thereof. Site-specific recombinases useful for creating the chimeric recombinases of the invention, include recombinases from the integrase family, derivatives thereof, and any other naturally occurring or recombinantly produced enzyme or derivative thereof, that catalyzes conservative site-specific recombination between specified DNA sites. The integrase family of recombinases has over thirty members and includes FLP, Cre, Int and R. Preferably, the recombinases do not require cofactors or a supercoiled substrate. Most preferably the recombinases are Cre and FLP. The bacteriophage P1 loxP-Cre and the Saccharomyces $2\mu$ plasmid FRT/FLP site-specific recombinations systems have been extensively studied and their uses are well known to those skilled in the art. Cre and FLP are known to function in a variety of organisms, including bacteria, yeast, Drosophila, mammals and monocotyledonous and dicotyledonous plants. In addition these recombinases do not require auxiliary factors to function.

The site-specific recombinases and sequences encoding them that are used in the methods and compositions of the invention may be variants of naturally occurring recombinases and the genes encoding them. The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of fuinctionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. One of ordinary skill will recognize that each codon in a nucleic acid (except AUG, which is ordinarily the only codon for methionine) can be modified to yield a functionally identical molecule.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).

See Creighton (1984) *Proteins,* W. H. Freeman and Company.

Rather than use full length recombinases, fuinctional fragments of site-specific recombinases may be used in the methods and compositions of the invention. Functional fragments of site-specific recombinases can be identified using a variety of techniques. For example, functional fragments of the FLP protein may be identified by their ability, upon introduction to cells containing appropriate FRT substrates, to catalyze site-specific recombination and result in the excision of an assayable marker gene.

A general approach of such functional analysis involves subcloning DNA fragments of a genomic clone, cDNA clone or synthesized gene sequence into an expression vector, introducing the expression vector into a heterologous host, and screening to detect the product of recombination (i.e. using restriction analysis to verify the product of recombination at the nucleic acid level, or relying on an assay system for recombination as described above). Methods for generating fragments of a cDNA or genomic clone are well known. Variants of an isolated DNA encoding a site-specific recombinase can be produced by deleting, adding and/or substituting nucleotides. Such variants can be obtained, for example, by oligonucleotide-directed mutagenesis, linker-scanning mutagenesis, mutagenesis using the polymerase chain reaction, and the like. See, for example, Ausubel, *Current Protocols In Molecular Biology,* Wiley Interscience (1990) pages 8.0.3–8.5.9, and McPherson (ed.), *Directed Mutagenesis: A Practical Approach,* (IRL Press, 1991).

The dual function recombinant proteins of the invention comprise a first site-specific recombinase fused in frame with a second site-specific recombinase. It will be recognized that in the methods of invention, the recombinases comprising the chimeric recombinase must correspond to the target sites of the transformed organism and the targeting cassette. That is, if FRT and loxP sites are utilized, a chimeric FLP:Cre recombinase will be needed.

The open reading frames encoding the first and second recombinases may be directly fused to each other or may be joined by a linker that maintains the correct reading frame of the chimeric recombinase. It is understood that the recombinases may be fused amino to carboxy terminus, amino to amino terminus, or carboxy to amino terminus.

Genes encoding chimeric site-specific recombinases and recombination sites can be made using standard recombinant methods, synthetic techniques, or combinations thereof Use of cloning vectors, expression vectors, adapters, and linkers is well known in the art and can be found in such references as Sambrook et al., *Molecular Cloning: A Laboratory Manual,* 2nd ed. (Cold Spring Harbor, N.Y., 1989). A variety of strategies are available for ligating fragments of DNA, the choice of which depends on the nature of the termini of the DNA fragments and which choices can be readily made by those of skill in the art. The FLP recombinase gene from yeast (*Saccharomyces cerevisiae*) is commercially available in plasmid pOG44 from Stratagene Cloning Systems (11011 North Torrey Pines Road, La Jolla, Calif. 92037). For a description of the FLP gene and various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.). Similarly, the sequences of many other site specific recombinases and their cognate recombination sites are publicly or commercially available. Genes encoding FLP and Cre can also be obtained, for example, by synthesizing the genes with mutually priming long oligonucleotides. See, for example, Ausubel et al. (eds.), *Current Protocols In Molecular Biology,* pages 8.2.8 to 8.2.13, Wiley Interscience (1990). Also, see Wosniak et al. (1987) *Gene* 60:115. Moreover, current techniques using the polymerase chain reaction provide the ability to synthesize genes as large as 1.8 kilobases in length (Adang et al. (1993) *Plant Mol. Biol.* 21:1 131; Bombat et al. (1993) *PCR Methods and Applications* 2:266).

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucl. Acids Res.* 17:477–498; and Campbell et al. (1990) *Plant Physiol.* 92:1). Thus, the maize preferred codon for a particular amino acid may be derived from known gene sequences from maize. Maize codon usage for 28 genes from maize plants are listed in Table 4 of Murray et al., supra.

Examples of genes encoding recombinases, using maize preferred codons include, FLPm, described in co-pending application Ser. No. 08/972,258; the contents of which are incorporated herein by reference, and moCre, shown in SEQ. ID NOS. 1 and 2. FLPm is derived from the Saccharomyces 2$\mu$ plasmid FLP recombinase, but is encoded by a nucleic acid sequence utilizing maize-preferred codons. While the FLPm nucleic acid sequence includes preferred codons for expression of amino acids in maize, it is understood that a useful sequence may contain codons occurring in maize with less than the highest reported maize codon frequencies. Examples of nucleic acids encoding chimeric recombinases include Cre:FLPm (SEQ. ID NO. 4), moCre:FLPm (SEQ. ID NO. 5), Cre:FLP (SEQ. ID NO. 7) and FLPm:Cre (SEQ. ID NO. 8).

The invention also provides expression cassettes containing a nucleic acid sequence encoding a chimeric site-specific recombinase, operably linked to a promoter that drives expression in a eukaryotic cell. Preferably the promoter is a plant promoter. For example, the plant expression vector PHP13147, shown in FIG. 1, contains an expression cassette for Cre:FLPm, wherein the gene encoding the chimeric recombinase is operably linked to a ubiquitin promoter. As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria genes that are expressed in plant cells such as those of Agrobacterium or Rhizobium. Both heterologous and non-heterologous (i.e., endogenous) promoters can be employed to direct expression of a sequence encoding a site-specific recombinase. The promoter may be constitutive, inducible or tissue specific.

Many different constitutive promoters can be utilized in the instant invention. Exemplary constitutive promoters include the promoters from plant viruses such as the 35S promoter from CaMV (Odell et al. (1985) *Nature* 313:810–812) and the promoters from such gene as rice actin (McElroy et al. (1990) *Plant Cell* 2:163–171), ubiquitin (Christensen et al. (1989) *Plant Mol. Biol.* 12:619–632 and Christensen et al. (1992) *Plant Mol. Biol.* 18:675–689), pEMU (Last et al. (1991) *Theor. Appl. Genet.* 81:581–588); MAS (Velten et al. (1984) *EMBO J.* 3:2723–2730), maize H3 histone (Lepetit et al. (1992) *Mol. Gen. Genet.* 231: 276–285 and Atanassova et al. (1992) *Plant Journal* 2(3):291–300); the 1'- or 2'- promoter derived from T-DNA of *Agrobacterium tumefaciens*, the Smas promoter, the cinnamyl alcohol dehydrogenase promoter (U.S. Pat. No. 5,683,439), the Nos promoter, the Pemu promoter, the rubisco promoter, the GRP1-8 promoter, and other transcription initiation regions from various plant genes known to those of skill. The ALS promoter, a XbaI/NcoI fragment 5-prime to the *Brassica napus* ALS3 structural gene (or a nucleotide sequence that has substantial sequence similarity to said XbaI/NcoI fragment), represents a particularly useful constitutive promoter. (See co-pending Pioneer Hi-Bred International U.S. patent application Ser. No. 08/409,297, the contents of which are incorporated by reference).

A variety of inducible promoters can be used in the instant invention. See Ward et al. (1993) *Plant Mol. Biol.* 22:361–366. Exemplary inducible promoters include that from the ACE1 system which responds to copper (Mett et al. (1993) *PNAS* 90:4567–4571); In2 gene from maize which responds to benzenesulfonamide herbicide safeners (Hershey et al. (1991) *Mol. Gen. Genetics* 227:229–237 and Gatz et al. (1994) *Mol. Gen. Genetics* 243:32–38), the Adh1 promoter which is inducible by hypoxia or cold stress, the Hsp70 promoter which is inducible by heat stress, and the PPDK promoter which is inducible by light; or Tet repressor from Tn10 (Gatz et al. (1991) *Mol. Gen. Genet.* 227:229–237. A particularly preferred inducible promoter is a promoter that responds to an inducing agent to which plants do not normally respond. An exemplary inducible promoter is the inducible promoter from a steroid hormone gene the transcriptional activity of which is induced by a glucocorticosteroid hormone (Schena et al. (1991) *Proc. Natl. Acad. Sci. U.S.A.* 88:10421).

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

The chimeric recombinase must be expressed in the plant cell in order for integration of the DNA of interest into the host chromosome. Accordingly, the expression cassette encoding the site-specific recombinase may be supplied in cis to the DNA of interest; in trans on a host chromosome or extrachromosomal replicon; or may be transferred to the host and transiently expressed near to the time that recombination is desired.

The compositions of the invention include transfer cassettes comprising nucleotide sequences encoding the chimeric recombinases of the invention. By transfer cassette is meant any nucleotide sequence that may be used to transform a cell of interest. For example, the transfer cassette may be an independent replicon such as a plasmid, shuttle vector, Ti plasmid, viral vector or the like. Alternatively, the transfer cassette could be a nucleic acid that is not capable of independent replication, yet could be transferred into an organism of interest by a variety of transformation protocols, such as particle bombardment, electroporation, and the like. Thus, the invention provides a transfer cassette comprising a nucleotide sequence encoding a recombinant protein comprising a first site-specific recombinase fused in frame with a second site-specific recombinase, wherein said nucleotide sequence is operably linked to a promoter that drives expression in a eukaryotic cell.

In the compositions and methods of the invention, the DNA of interest is flanked by target sites for two distinct site-specific recombinases. By "flanked by" is meant that the recombination or target sites may be directly contiguous with the DNA of interest, or there may be one or more intervening sequences present between one or both ends of the DNA of interest and the site specific recombination sites. Intervening sequences of particular interest would include linkers, adapters, selectable markers and/or other sites which aid in vector construction or analysis and expression cassette for a gene of interest. Target sites for site-specific recombinases are known to those skilled in the art and are discussed in co-pending provisional application No. 60/065,613. Examples of target sites include, but are not limited to FRT, FRT1, FRT5, FRT6, FRT7, other FRT mutants, loxP, loxP mutants, and the like. See, for example, Schlake and Bode (1994) *Biochemistry* 33:12746–12751; Huang et al. (1991) *Nucleic Acids Research* 19:443–448; Sadowski (1995) In *Progress in Nucleic Acid Research and Molecular Biology* 51:53–91; Cox (1989) In *Mobile DNA*, Berg and Howe (eds) American Society of Microbiology, Washington D.C., pp. 116–670, Dixon et al. (1995) *Mol. Microbio.* 18:449–458; Umlauf and Cox (1988) *EMBO J.* 7:1845–1852; Buchholz et al. (1996) *Nuc. Acids Res.* 24:3118–3119; Kilby et al. (1993) *Trends Genet.* 9:413–42 1: Rossant and Geagy (1995) *Nat. Med.* 1: 592–594, Lox Albert et al. (1995) *Plant J.* 7:649–659: Bayley et al. (1992) *Plant Mol. Biol.* 18:353–361; Odell et al. (1990) *Mol. Gen. Genet.* 223:369–378; and Dale and Ow (1991) *Proc. Natl. Acad. Sci. USA* 88:10558–105620; Qui et al. (1994) *Proc. Natl. Acad. Sci. USA* 91:1706–171 0; Stuurman et al. (1996) *Plant Mol. Biol.* 32:901–913; and Dale et al. (1990) *Gene* 91:79–85; all of which are herein incorporated by reference.

By "target site for a site-specific recombinase" is meant a DNA sequence that is recognized by a particular site-specific recombinase. A variety of recombination sites are known to those skilled in the art and may be used in the methods and compositions of the invention. The site may have the sequence of the cognate site for a given recombinase, or may be modified, so long as it is capable of acting as a recombination site. The site may be contain the minimal sequences necessary for recombination, or it may contain additional sequences that enhance recombination. Examples of recombination sites for use in the invention are known in the art and include FRT and loxp sites (See, for example, Schlake et al. (1994) *Biochemistry* 33:12746–1275 1; Huang et al. (1991) *Nucleic Acids Research* 19:443–448; Sadowski, Paul D. (1995) In *Progress in Nucleic Acid Research and Molecular Biology* 51: 53–91; Cox, Michael M. (1989) In *Mobile DNA*, Berg and Howe (eds) American Society of Microbiology, Washington D.C., pp. 116–670; Dixon et al. (1995) *Mol. Microbio.* 18.449–458; Umlaufet et al. (1988) *EMBO J.* 7:1845–1852; Buchholz et al. (1996) *Nuc. Acids Res.* 24:3118–3119, Kilby et al. (1993) *Trends Genet.* 9:413–421: Rossant et al. (1995) *Nat. Med.* 1: 592–594, Lox Albert et al. (1995) *Plant J.* 7:649–659: Bayley et al. (1992) *Plant Mol. Biol.* 18:353–361; Odell et al. (1990) *Mol. Gen. Genet.* 223:369–378, and Dale et al. (1991) *Proc. Natl. Acad. Sci. USA* 88:10558–105620; Qui et al. (1994) *Proc. Natl. Acad. Sci. USA* 91:1706–1710, Stuurman et al. (1996)

*Plant Mol. Biol.* 32:901–913; Hartley et al. (1980) *Nature* 286: 860–864; Sauer (1994) *Current Opinion in Biotechnology* 5:521–527; and Dale et al. (1990) *Gene* 91:79–85; all of which are herein incorporated by reference.)

Each loxP and FRT site contains two 13 base pair inverted repeats which flank an 8 base pair spacer. The FRT site contains an additional non-essential 13 base pair repeat. The sequences of the loxP and FRT sites have been described in many publications. A minimal FRT site (SEQ ID NO: 10)comprising two 13 base pair repeats, separated by an 8 base spacer, is:

5'-GAAGTTCCTATTC[TCTAGAAA]
GTATAGGAACTTC3' wherein the nucleotides within the brackets indicate the spacer region. The nucleotides in the spacer region can be replaced with a combination of nucleotides, so long as the two 13-base repeats are separated by eight nucleotides. FLP is a conservative, site-specific recombinase, capable of catalyzing inversion of a nucleic acid sequence positioned between two inversely oriented FRTs; recombination between two molecules each containing a FRT site; and excision between FRT sites. The core region is not symmetrical, and its asymmetry dictates the directionality of the reaction. Recombination between inverted FRT sites causes inversion of a DNA sequence between them, whereas recombination between directly oriented sites leads to excision of the DNA between them.

Nucleotide sequences containing a DNA of interest flanked by target sites, transfer cassettes for two distinct site-specific recombinases and vectors carrying these sequences may be constructed using standard molecular biology techniques. See, for example, Sambrook et al. (eds.) Molecular Cloning: A Laboratory Manual, Second Edition, (Cold Spring Harbor Laboratory Press, cold Spring Harbor, N.Y. 1989).

Techniques for transforming a wide variety of eukaryotic cells, including higher plant species are well known and described in the technical, scientific, and patent literature. See, for example, Weising et al. (1988) *Ann. Rev. Genet.* 22: 421–477. These methods are useful for transforming a plant cell with the chimeric recombinase expression cassettes of the invention and DNAs of interest flanked by target sites for the chimeric recombinase. The expression cassette encoding the site-specific recombinase may be present in the plant genome prior to transformation of the DNA of interest, or may be transformed into the plant around the time of transformation with the T-DNA to the plant cell so that it will be transiently expressed. For example, the DNA construct may be introduced directly into the genomic DNA of the plant cell using techniques such as electroporation, PEG poration, particle bombardment, silicon fiber delivery, or microinjection of plant cell protoplasts or embryogenic callus.

*Agrobacterium tumefaciens*-meditated transformation techniques are well described in the scientific literature. See, for example Horsch et al, *Science* 233: 496–498 (1984), Fraley et al. (1983) *Proc. Natl. Acad. Sci.* 80:4803 and Kado, (1991), *Crit. Rev. Plant Sci.* 10:1. Descriptions of the Agrobacterium vector systems and methods for Agrobacterium-mediated gene transfer are provide in Gruber et al., supra, Miki, et al., supra; and Moloney et al. (1989), *Plant Cell Reports* 8:238. Although Agrobacterium is useful primarily in dicots, certain monocots can be transformed by Agrobacterium. For instance, Agrobacteriurm transformation of maize is described in U.S. Pat. No. 5,550, 318. Other methods of agroinfection include *Agrobacterium rhizogenes*-mediated transformation (see, e.g., Lichtenstein and Fuller In: *Genetic Engineering, vol.* 6, P W J Rigby, Ed., London, Academic Press, 1987; and Lichtenstein, C. P., and Draper, J,. In: *DNA Cloning, Vol. II,* D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16.

Optimized methods and vectors for Agrobacterium-mediated transformation of plants in the family Graminae, such as rice and maize have been described by Heath et al. (1997) *Mol. Plant-Microbe Interact.* 10:221–227; Hiei et al. (1994) *Plant J.* 6:271–282 and Ishida et al. (1996) *Nat. Biotech.* 14:745–750, the contents of which are incorporated herein by reference. The efficiency of maize transformation is affected by a variety of factors including the types and stages of tissue infected, the concentration of Agrobacterizum, the tissue culture media, the Ti vectors and the maize genotype. Super binary vectors carrying the vir genes of Agrobacterium strains A281 and A348 are useful for high efficiency transformation of monocots.

The introduction of DNA constructs using polyethylene glycol precipitation is described in Paszkowski et al. (1984) *Embo J.* 3: 2717–2722. Electroporation techniques are described in Fromm et al. (1985) *Proc. Natl. Acad. Sci.* 82: 5824. Ballistic transformation techniques are described in Klein et al. (1987) *Nature* 327: 70–73.

Viral means of introducing DNA into mammalian cells are known in the art. In particular, a number of vector systems are known for the introduction of foreign or native genes into mammalian cells. These include SV40 virus (See, e.g., Okayama et al. (1985) *Molec. Cell Biol.* 5:1136–1142), Bovine papilloma virus (See, e.g., DiMaio et al. (1982) *Proc. Natl. Acad. Sci. USA* 79:4030–4034); adenovirus (See, e.g., Morin et al. (1987) *Proc. Natl. Acad. Sci. USA* 84:4626; Yifan et al. (1995) *Proc. Natl. Acad. Sci. USA* 92:1401–1405; Yang et al. (1996) *Gene Ther.* 3:137–144; Tripathy et al. (1996) *Nat. Med.* 2:545–550; Quantin et al. (1992) *Proc. Natl. Acad. Sci. USA* 89:2581–2584; Rosenfeld et al. (1991) *Science* 252:431–434; Wagner (1992) *Proc. Natl. Acad. Sci. USA* 89:6099–6103; Curiel et al. (1992) *Human Gene Therapy* 3:147–154; Curiel (1991) *Proc. Natl. Acad. Sci. USA* 88:8850–8854; LeGal LaSalle et al. (1993) *Science* 259:590–599); Kass-Eisler et al. (1993) *Proc. Natl. Acad. Sci. USA* 90:11498–11502), adeno-associated virus (See, e.g., Muzyczka et al. (1994) *J. Clin. Invest.* 94:13 5 1; Xiao et al. (1996) *J. Virol.* 70:8098–8108); herpes simplex virus (See, e.g., Geller et al. (1988) *Science* 241:1667; Huard et al. (1995) *Gene Therapy* 2:385–392, U.S. Pat. No. 5,501, 979), retrovirus-based vectors (See, for example, Curran et al. (1982) *J. Virol.* 44:674–682; Gazit et al. (1986) J. Virol. 60: 19–28; Miller, A. D. (1992) *Curr. Top. Microbiol. Immunol.* 158:1–24; Cavanaugh et al. (1994) *Proc. Natl. Acad. Sci. USA* 91:7071–7075; Smith et al. (1990) *Molecular and Cellular Biology* 10:3268–3271); herein incorporated by reference. See also, Wu et al. (1991) *J. Biol. Chem.* 266:14338–14342, Wu et al. (1988) *J. Biol Chem.* 263:14621–14624; Wu et al. (1989) *J. Biol Chem.* 264:16985–16987; Zenke et al. (1990) *Proc. Natl. Acad. Sci. USA* 87:3655–3659; Wagner et al. (1990) *Proc. Natl. Acad. Sci. USA* 87:3410–3414.

DNA can also be introduced into plants by direct DNA transfer into pollen as described by Zhou et al. (1983) *Methods in Enzymology,* 101:433; D. Hess, (1987) *Intern Rev. Cytol.,* 107:367; Luo et al. (1988) *Plane Mol. Biol. Reporter* 6:165. Expression of polypeptide coding genes can be obtained by injection of the DNA into reproductive organs of a plant as described by Pena et al. (1987) *Nature*

325:274. DNA can also be injected directly into the cells of immature embryos and the rehydration of desiccated embryos as described by Neuhaus et al. (1987) *Theor. Appl. Genet.* 75:30; and Benbrook et al. (1986) *Proceedings Bio Expo,* Butterworth, Stoneham, Mass., pp. 27–54. A variety of plant viruses that can be employed as vectors are known in the art and include cauliflower mosaic virus (CaMV), geminivirus, brome mosaic virus, and tobacco mosaic virus.

Plants cells stably transformed with a chimeric recombinase expression cassette can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al. (1983) *Protoplasis Isolation and Culture, Handbook of Plant Cell Culture,* Macmillilan Publishing Company, New York, pp. 124–176; and Binding (1985) *Regeneration of Plants, Plant Protoplasts,* CRC Press, Boca Raton, pp. 21–73.

The regeneration of plants containing the recombinant genes can be achieved as described by Horsch et al. (1985) *Science,* 227:1229–1231. In this procedure, transformants are grown in the presence of a selection agent and in a medium that induces the regeneration of shoots in the plant species being transformed as described by Fraley et al. (1983) *Proc. Natl. Acad. Sci. USA* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof Such regeneration techniques are described generally in Klee et al. (1987) *Ann. Rev. of Plant Phys.* 38: 467–486. The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook,* Freeling and Walbot, Eds., Springer, New York (1994); *Corn and Corn Improvement,* 3rd edition, Sprague and Dudley Eds., American Society of Agronomy, Madison, Wis. (1988).

One of skill will recognize that after a DNA, such as a chimeric recombinase expression cassette or target site for a chimeric recombinase is stably incorporated in transgenic plants and confirmed to be operable, it can be introduced into other plants by sexual crossing. Any of a number of standard breeding techniques can be used, depending upon the species to be crossed.

The methods and compositions of the invention are useful to integrate a DNA of interest into the genome of any host cell, including any plant host. As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred monocot is maize. Other monocots of particular interest include wheat, rice, barley, sorghum and rye. Dicots of particular interest include soybean, Brassica, sunflower, alfalfa, and safflower.

Because of the use of the chimeric site-specific recombinases and target sites provided herein, the cells transformed by the methods of the invention may be distinguishable from other transformation methods as the modified cells of the invention will contain nucleotide sequences of interest inserted into the genome flanked by target sites for distinct recombinases.

The following examples are offered by way of illustration not by way of limitation.

EXPERIMENTAL

EXAMPLE 1

Construction of Vectors Containing a DNA of Interest Flanked By Target Sites For a Chimeric Site-Specific Recombinase DNA fragments containing a DNA of interest flanked by loxP and FRT target sites are constructed either by synthesizing, annealing and ligating complementary oligonucleotides or by creating primers for PCR amplification of a DNA of interest with containing the loxp and bRT sites in addition to restriction sites useful for cloning into a vector of choice.

For example, long PCR primers may be designed wherein the 3' end of the primer hybridizes to the 5' end of the DNA of interest and the 5' end of the primers further contain loxP or FRT sites and useful cloning sites. The resulting PCR product is digested with the appropriate restriction enzyme and inserted into an appropriate vector,

EXAMPLE 2

Excision of FRT Site by FLPm and the Cre:FLPm Chimeric Recombinase

Figure 2:
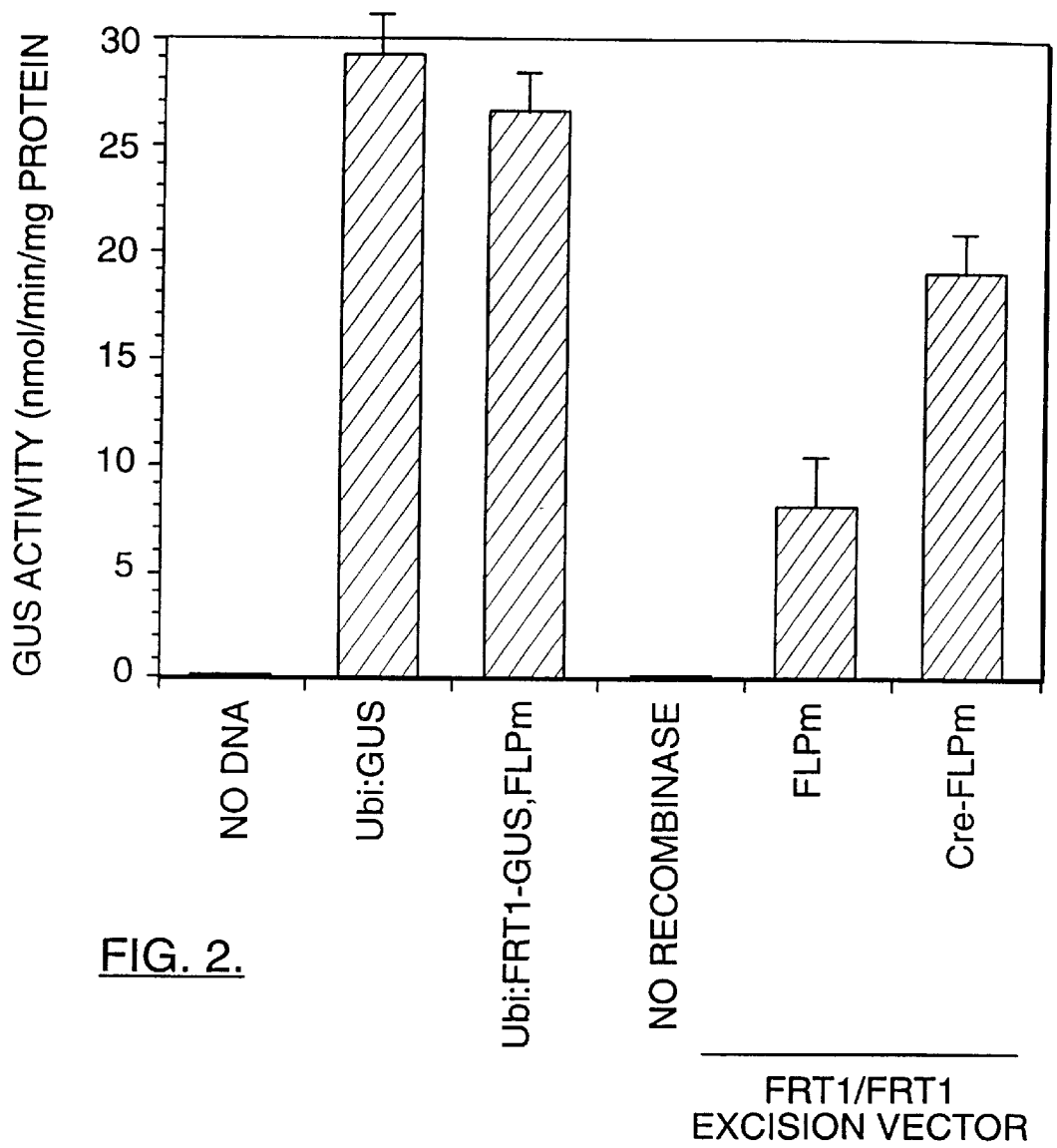
FIG. 2 graphically represents activation of GUS expression by FLPm or CRE:FLPm mediated excision of a sequence flanked by FRT sites that separates the ubiquitin promoter and the GUS open reading frame.
Figure 3:
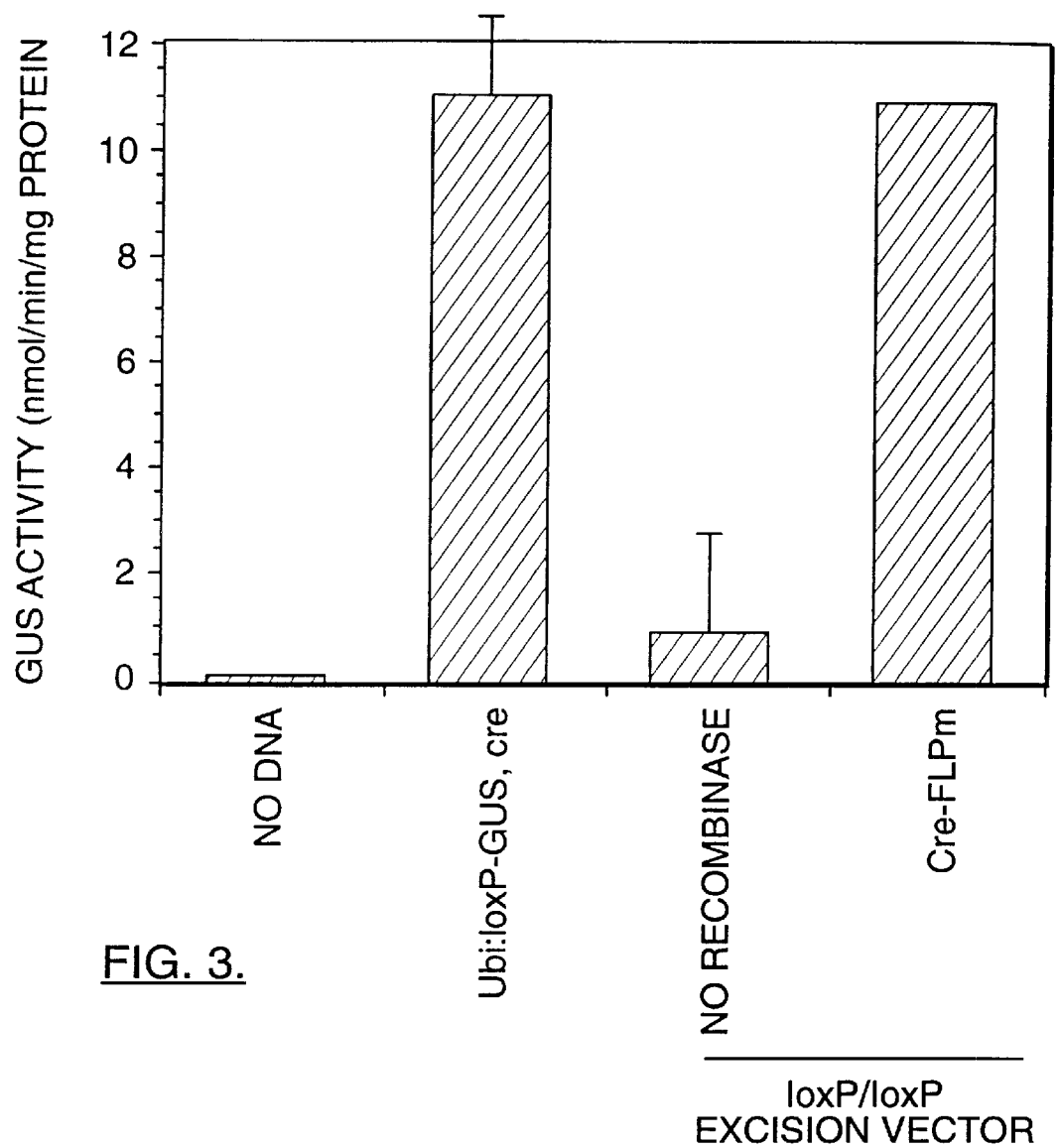
FIG. 3 graphically represents activation of GUS expression by CRE:FLPm mediated excision of a sequence flanked by loxP sites that separates the ubiquitin promoter and the GUS open reading frame.

A transfer cassette encoding a Cre-FLPm chimeric recombinase was transformed into plant cells having an expression cassette encoding GUS driven by the ubiquitin promoter, wherein a sequence flanked by either identical FRT or loxP sites interrupted the GUS open reading frame. FIGS. 2 and 3 show that the Cre-FLPm chimeric recombinase is functional independently at either the FRT site or the loxP site, as measured by the ability to activate GUS activity following excision of sequences between two identical target sites, thereby bringing GUS activity under the control of the ubiquitin promoter.

All publications and patent applications mentioned in the specification are indicative of the level of those skilled in the aft to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant protein comprising: a first site-specific recombinase fused in frame with a second site-specific recombinase.

2. A recombinant protein comprising a first site-specific recombinase or an active variant or an active fragment thereof fused in frame with a second site-specific recombinase or an active variant or an active fragment thereof, wherein said active variant and said active fragment retain site-specific recombinase activity.

3. The recombinant protein of claim 2, wherein said first and said second site-specific recombinases are members of the integrase family of recombinases or an active variant and an active fragment thereof, wherein said active variant and said active fragment retain site-specific recombinase activity.

4. The recombinant protein of claim 3, wherein said first and said second recombinases are selected from the group consisting of Cre, FLP and an active variant and an active fragment thereof, wherein said active variant and said active fragment retain site-specific recombinase activity.

5. The recombinant protein of claim 4, comprising the amino acid sequence of SEQ ID NO: 3 or an active variant or an active fragment thereof, wherein said active variant or said active fragment retains site-specific recombinase activity.

6. The recombinant protein of claim 4, wherein said first recombinase is Cre or an active variant or an active fragment thereof, and said second recombinase is FLP or an active variant or an active fragment thereof, wherein said active variant and said active fragment retain site-specific recombinase activity.

7. The recombinant protein of claim 6, wherein the Cre recombinase is moCre.

8. The recombinant protein of claim 6, wherein the FLP recombinase is FLPm.

9. The recombinant protein of claim 4, wherein said first recombinase is FLP or an active variant or an active fragment thereof, and said second recombinase is Cre or an active variant or an active fragment thereof, wherein said active variant and said active fragment retain site-specific recombinase activity.

10. The recombinant protein of claim 9, wherein the FLP recombinase is FLPm.

11. The recombinant protein of claim 9, wherein the Cre recombinase is moCre.

12. The recombinant protein of claim 4, comprising the amino acid sequence of SEQ ID NO:9 or an active variant or an active fragment thereof, wherein said active variant or said active fragment retains site-specific recombinase activity.

13. The recombinant protein of claim 1, wherein said first and said second site-specific recombinaes are selected from the group consisting of Cre and FLP.

14. A recombinant protein comprising the amino acid sequence of SEQ ID NO:3.

15. A recombinant protein comprising the amino acid sequence of SEQ ID NO: 9.

* * * * *

UNITED STATES PATENT AND TRADEMARK OFFICE
CERTIFICATE OF CORRECTION

PATENT NO.      : 6,541,231 B1
DATED           : April 1, 2003
INVENTOR(S)     : Baszczynski et al.

It is certified that error appears in the above-identified patent and that said Letters Patent is hereby corrected as shown below:

<u>Title page,</u>
Item [75], Inventors, the address of inventor "Laura A. Tagliani" should read -- Zionsville, IN --.

Signed and Sealed this

Ninth Day of September, 2003

JAMES E. ROGAN
*Director of the United States Patent and Trademark Office*

SEQUENCE LISTING

<160> NUMBER OF SEQ ID NOS: 11

<210> SEQ ID NO 1
<211> LENGTH: 343
<212> TYPE: PRT
<213> ORGANISM: Artificial Sequence
<220> FEATURE:
<223> OTHER INFORMATION: Description of Artificial Sequence: Cre protein
      from Bacteriophage P1 with maize preferred codons
      (moCRE)

<400> SEQUENCE: 1

Met Ser Asn Leu Leu Thr Val His Gln Asn Leu Pro Ala Leu Pro Val
 1               5                  10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

```
Arg Leu Leu Glu Asp Gly Asp
            340

<210> SEQ ID NO 2
<211> LENGTH: 1032
<212> TYPE: DNA
<213> ORGANISM: Artificial Sequence
<220> FEATURE:
<223> OTHER INFORMATION: Description of Artificial Sequence: Nucleotide
      sequence encoding Cre protein from Bacteriophage
      P1, maize preferred codons (moCRE)

<400> SEQUENCE: 2
atgtccaacc tgctcacggt tcaccagaac cttccggctc ttccagtgga cgcgacgtcc      60
gatgaagtca ggaagaacct catggacatg ttccgcgaca ggcaagcgtt cagcgagcac     120
acctggaaga tgctgctctc cgtctgccgc tcctgggctg catggtgcaa gctgaacaac     180
aggaagtggt tccccgctga gcccgaggac gtgagggatt accttctgta cctgcaagct     240
cgcgggctgg cagtgaagac catccagcaa caccttggac aactgaacat gcttcacagg     300
cgctccggcc tcccgcgccc cagcgactcg aacgccgtga gcctcgtcat cgccgcatc      360 aggaaggaaa acgtcgatgc cggcgaaagg gcaaagcagg ccctcgcgtt cgagaggacc     420
gatttcgacc aggtccgcag cctgatggag aacagcgaca ggtgccagga cattaggaac     480
ctggcgttcc tcggaattgc atacaacacg ctcctcagga tcgcggaaat tgcccgcatt     540
cgcgtgaagg acattagccg caccgacggc ggcaggatgc ttatccacat ggcaggacc      600 aagacgctcg tttccaccgc aggcgtcgaa aaggccctca gcctcggagt gaccaagctc     660
gtcgaacgct ggatctccgt gtccggcgtc gcggacgacc aaacaactca cctcttctgc     720
cgcgtccgca gaacgggggt ggctgccct agcgccacca gccaactcag cacgagggcc      780
ttggaaggta ttttcgaggc cacccaccgc ctgatctacg cgcgaaagga tgacagcggt     840
caacgctacc tcgcatggtc cgggcactcc gcccgcgttg gagctgctag ggacatggcc     900
cgcgccggtg tttccatccc cgaaatcatg caggcgggtg gatggacgaa cgtgaacatt     960
gtcatgaact acattcgcaa ccttgacagc gagacgggcg caatggttcg cctcctggaa    1020
gatggtgact ga                                                         1032

<210> SEQ ID NO 3
<211> LENGTH: 781
<212> TYPE: PRT
<213> ORGANISM: Artificial Sequence
<220> FEATURE:
<223> OTHER INFORMATION: Description of Artificial Sequence: Cre:FLPm
      polypeptide, Cre from Bacteriophage P1 and FLP
      from Saccharomyces with maize preferred codons

<400> SEQUENCE: 3

Met Ala Asn Leu Leu Thr Val His Gln Asn Leu Pro Ala Leu Pro Val
 1               5                  10                  15

Asp Ala Thr Ser Asp Glu Val Arg Lys Asn Leu Met Asp Met Phe Arg
                20                  25                  30

Asp Arg Gln Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
        50                  55                  60

Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
```

```
                        85                  90                  95
Met Leu His Arg Arg Ser Gly Leu Pro Arg Pro Ser Asp Ser Asn Ala
                    100                 105                 110
Val Ser Leu Val Met Arg Arg Ile Arg Lys Glu Asn Val Asp Ala Gly
                115                 120                 125
Glu Arg Ala Lys Gln Ala Leu Ala Phe Glu Arg Thr Asp Phe Asp Gln
            130                 135                 140
Val Arg Ser Leu Met Glu Asn Ser Asp Arg Cys Gln Asp Ile Arg Asn
145                 150                 155                 160
Leu Ala Phe Leu Gly Ile Ala Tyr Asn Thr Leu Leu Arg Ile Ala Glu
                165                 170                 175
Ile Ala Arg Ile Arg Val Lys Asp Ile Ser Arg Thr Asp Gly Gly Arg
            180                 185                 190
Met Leu Ile His Ile Gly Arg Thr Lys Thr Leu Val Ser Thr Ala Gly
                195                 200                 205
Val Glu Lys Ala Leu Ser Leu Gly Val Thr Lys Leu Val Glu Arg Trp
        210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Glu Gly Ile Phe Glu Ala Thr His Arg Leu Ile
            260                 265                 270
Tyr Gly Ala Lys Asp Asp Ser Gly Gln Arg Tyr Leu Ala Trp Ser Gly
            275                 280                 285
His Ser Ala Arg Val Gly Ala Ala Arg Asp Met Ala Arg Ala Gly Val
        290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp Gly Gly Ser Gly Gly Gly Ser Gly
            340                 345                 350
Gly Gly Ser Asp Pro Thr Met Pro Gln Phe Asp Ile Leu Cys Lys Thr
            355                 360                 365
Pro Pro Lys Val Leu Val Arg Gln Phe Val Glu Arg Phe Glu Arg Pro
        370                 375                 380
Ser Gly Glu Lys Ile Ala Leu Cys Ala Ala Glu Leu Thr Tyr Leu Cys
385                 390                 395                 400
Trp Met Ile Thr His Asn Gly Thr Ala Ile Lys Arg Ala Thr Phe Met
                405                 410                 415
Ser Tyr Asn Thr Ile Ile Ser Asn Ser Leu Ser Phe Asp Ile Val Asn
            420                 425                 430
Lys Ser Leu Gln Phe Lys Tyr Lys Thr Gln Lys Ala Thr Ile Leu Glu
        435                 440                 445
Ala Ser Leu Lys Lys Leu Ile Pro Ala Trp Glu Phe Thr Ile Ile Pro
    450                 455                 460
Tyr Tyr Gly Gln Lys His Gln Ser Asp Ile Thr Asp Ile Val Ser Ser
465                 470                 475                 480
Leu Gln Leu Gln Phe Glu Ser Ser Glu Glu Ala Asp Lys Gly Asn Ser
            485                 490                 495
His Ser Lys Lys Met Leu Lys Ala Leu Leu Ser Glu Gly Glu Ser Ile
        500                 505                 510
```

```
Trp Glu Ile Thr Glu Lys Ile Leu Asn Ser Phe Glu Tyr Thr Ser Arg
        515                 520                 525

Phe Thr Lys Thr Lys Thr Leu Tyr Gln Phe Leu Phe Leu Ala Thr Phe
        530                 535                 540

Ile Asn Cys Gly Arg Phe Ser Asp Ile Lys Asn Val Asp Pro Lys Ser
545                 550                 555                 560

Phe Lys Leu Val Gln Asn Lys Tyr Leu Gly Val Ile Ile Gln Cys Leu
                565                 570                 575

Val Thr Glu Thr Lys Thr Ser Val Ser Arg His Ile Tyr Phe Phe Ser
                580                 585                 590

Ala Arg Gly Arg Ile Asp Pro Leu Val Tyr Leu Asp Glu Phe Leu Arg
        595                 600                 605

Asn Ser Glu Pro Val Leu Lys Arg Val Asn Arg Thr Gly Asn Ser Ser
        610                 615                 620

Ser Asn Lys Gln Glu Tyr Gln Leu Leu Lys Asp Asn Leu Val Arg Ser
625                 630                 635                 640

Tyr Asn Lys Ala Leu Lys Lys Asn Ala Pro Tyr Ser Ile Phe Ala Ile
                645                 650                 655

Lys Asn Gly Pro Lys Ser His Ile Gly Arg His Leu Met Thr Ser Phe
                660                 665                 670

Leu Ser Met Lys Gly Leu Thr Glu Leu Thr Asn Val Val Gly Asn Trp
        675                 680                 685

Ser Asp Lys Arg Ala Ser Ala Val Ala Arg Thr Thr Tyr Thr His Gln
        690                 695                 700

Ile Thr Ala Ile Pro Asp His Tyr Phe Ala Leu Val Ser Arg Tyr Tyr
705                 710                 715                 720

Ala Tyr Asp Pro Ile Ser Lys Glu Met Ile Ala Leu Lys Asp Glu Thr
                725                 730                 735

Asn Pro Ile Glu Glu Trp Gln His Ile Glu Gln Leu Lys Gly Ser Ala
                740                 745                 750

Glu Gly Ser Ile Arg Tyr Pro Ala Trp Asn Gly Ile Ile Ser Gln Glu
        755                 760                 765

Val Leu Asp Tyr Leu Ser Ser Tyr Ile Asn Arg Arg Ile
        770                 775                 780
```

<210> SEQ ID NO 4
<211> LENGTH: 2346
<212> TYPE: DNA
<213> ORGANISM: Artificial Sequence
<220> FEATURE:
<223> OTHER INFORMATION: Description of Artificial Sequence:Nucleotide
      sequence encoding a Cre:FLPm polypeptide, Cre
      from Bacteriophage P1 and FLP (Maize preferred
      codons) from Saccharomyces

<400> SEQUENCE: 4

```
atggccaatt tactgaccgt acaccaaaat ttgcctgcat taccggtcga tgcaacgagt    60
gatgaggttc gcaagaacct gatggacatg ttcaggatc gccaggcgtt ttctgagcat   120
acctggaaaa tgcttctgtc cgtttgccgg tcgtgggcgg catggtgcaa gttgaataac   180
cggaaatggt ttcccgcaga acctgaagat gttcgcgatt atcttctata tcttcaggcg   240
cgcggtctgg cagtaaaaac tatccagcaa catttgggcc agctaaacat gcttcatcgt   300
cggtccgggc tgccacgacc aagtgacagc aatgctgttt cactggttat gcggcggatc   360
cgaaaagaaa acgttgatgc cggtgaacgt gcaaaacagg ctctagcgtt cgaacgcact   420
```

```
gatttcgacc aggttcgttc actcatggaa aatagcgatc gctgccagga tatacgtaat    480
ctggcatttc tggggattgc ttataacacc ctgttacgta tagccgaaat tgccaggatc    540
agggttaaag atatctcacg tactgacggt gggagaatgt taatccatat tggcagaacg    600
aaaacgctgg ttagcaccgc aggtgtagag aaggcactta gcctgggggt aactaaactg    660
gtcgagcgat ggatttccgt ctctggtgta gctgatgatc cgaataacta cctgttttgc    720
cgggtcagaa aaatggtgt tgccgcgcca tctgccacca gccagctatc aactcgcgcc     780
ctggaaggga tttttgaagc aactcatcga ttgatttacg cgctaagga tgactctggt     840 cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
gtcatgaact atatccgtaa cctggatagt gaaacagggg caatggtgcg cctgctggaa   1020
gatggcgatg gtggcggcag cggtggcggc tccggcggtg gctcggatcc aacaatgccc   1080
cagttcgaca tcctctgcaa gacccccccc aaggtgctcg tgaggcagtt cgtggagagg   1140
ttcgagaggc cctccggcga gaagatcgcc ctctgcgccg ccgagctcac ctacctctgc   1200
tggatgatca cccacaacgg caccgccatt aagagggcca ccttcatgtc atacaacacc   1260
atcatctcca actccctctc cttcgacatc gtgaacaagt ccctccagtt caaatacaag   1320
acccagaagg ccaccatcct cgaggcctcc ctcaagaagc tcatcccgc ctgggagttc    1380 accatcatcc cctactacgg ccagaagcac cagtccgaca tcaccgacat cgtgtcatcc   1440
ctccagcttc agttcgagtc ctccgaggag gctgacaagg caactccca ctccaagaag    1500 atgctgaagg ccctcctctc cgagggcgag tccatctggg agatcaccga gaagatcctc   1560
aactccttcg agtacacctc caggttcact aagaccaaga ccctctacca gttcctcttc   1620
ctcgccacct tcatcaactg cggcaggttc tcagacatca gaacgtgga ccccaagtcc    1680 ttcaagctcg tgcagaacaa gtacctcggc gtgatcatcc agtgcctcgt gaccgagacc   1740
aagacctccg tgtccaggca catctacttc ttctccgctc gcggcaggat cgacccctc    1800 gtgtacctcg acgagttcct caggaactca gagcccgtgc tcagagggt gaacaggacc    1860 ggcaactcct cctccaacaa gcaggagtac cagctcctca ggacaacct cgtgaggtcc    1920 tacaacaagg ccctcaagaa gaacgcccc tactccatct cgccatcaa gaacggcccc     1980 aagtcccaca tcggtaggca cctcatgacc tccttcctct caatgaaggg cctcaccgag   2040
ctcaccaacg tggtgggcaa ctggtccgac aagagggcct ccgccgtggc caggaccacc   2100
tacacccacc agatcaccgc catccccgac cactacttcg ccctcgtgtc aaggtactac   2160
gcctacgacc ccatctccaa ggagatgatc gccctcaagg acgagactaa ccccatcgag   2220
gagtggcagc acatcgagca gctcaagggc tccgccgagg gctccatcag gtaccccgcc   2280
tggaacggca tcatctccca ggaggtgctc gactacctct cctcctacat caacaggagg   2340
atctga                                                              2346
```

<210> SEQ ID NO 5
<211> LENGTH: 2346
<212> TYPE: DNA
<213> ORGANISM: Artificial Sequence
<220> FEATURE:
<223> OTHER INFORMATION: Description of Artificial Sequence: sequence encoding moCre:FLPm, Cre from Bacteriophage P1 and FLP from Saccharomyces, both maize preferred codons
<220> FEATURE:
<221> NAME/KEY: CDS
<222> LOCATION: (1)..(2346)

<400> SEQUENCE: 5

```
atg tcc aac ctg ctc acg gtt cac cag aac ctt ccg gct ctt cca gtg      48
Met Ser Asn Leu Leu Thr Val His Gln Asn Leu Pro Ala Leu Pro Val
 1               5                  10                  15 gac gcg acg tcc gat gaa gtc agg aag aac ctc atg gac atg ttc cgc      96
Asp Ala Thr Ser Asp Glu Val Arg Lys Asn Leu Met Asp Met Phe Arg
            20                  25                  30 gac agg caa gcg ttc agc gag cac acc tgg aag atg ctg ctc tcc gtc     144
Asp Arg Gln Ala Phe Ser Glu His Thr Trp Lys Met Leu Leu Ser Val
        35                  40                  45 tgc cgc tcc tgg gct gca tgg tgc aag ctg aac aac agg aag tgg ttc     192
Cys Arg Ser Trp Ala Ala Trp Cys Lys Leu Asn Asn Arg Lys Trp Phe
 50                  55                  60 ccc gct gag ccc gag gac gtg agg gat tac ctt ctg tac ctg caa gct     240
Pro Ala Glu Pro Glu Asp Val Arg Asp Tyr Leu Leu Tyr Leu Gln Ala
 65                  70                  75                  80 cgc ggg ctg gca gtg aag acc atc cag caa cac ctt gga caa ctg aac     288
Arg Gly Leu Ala Val Lys Thr Ile Gln Gln His Leu Gly Gln Leu Asn
                85                  90                  95 atg ctt cac agg cgc tcc ggc ctc ccg cgc ccc agc gac tcg aac gcc     336
Met Leu His Arg Arg Ser Gly Leu Pro Arg Pro Ser Asp Ser Asn Ala
            100                 105                 110 gtg agc ctc gtc atg cgc cgc atc agg aag gaa aac gtc gat gcc ggc     384
Val Ser Leu Val Met Arg Arg Ile Arg Lys Glu Asn Val Asp Ala Gly
        115                 120                 125 gaa agg gca aag cag gcc ctc gcg ttc gag agg acc gat ttc gac cag     432
Glu Arg Ala Lys Gln Ala Leu Ala Phe Glu Arg Thr Asp Phe Asp Gln
130                 135                 140 gtc cgc agc ctg atg gag aac agc gac agg tgc cag gac att agg aac     480
Val Arg Ser Leu Met Glu Asn Ser Asp Arg Cys Gln Asp Ile Arg Asn
145                 150                 155                 160 ctg gcg ttc ctc gga att gca tac aac acg ctc ctc agg atc gcg gaa     528
Leu Ala Phe Leu Gly Ile Ala Tyr Asn Thr Leu Leu Arg Ile Ala Glu
                165                 170                 175 att gcc cgc att cgc gtg aag gac att agc cgc acc gac ggc ggc agg     576
Ile Ala Arg Ile Arg Val Lys Asp Ile Ser Arg Thr Asp Gly Gly Arg
            180                 185                 190 atg ctt atc cac att ggc agg acc aag acg ctc gtt tcc acc gca ggc     624
Met Leu Ile His Ile Gly Arg Thr Lys Thr Leu Val Ser Thr Ala Gly
        195                 200                 205 gtc gaa aag gcc ctc agc ctc gga gtg acc aag ctc gtc gaa cgc tgg     672
Val Glu Lys Ala Leu Ser Leu Gly Val Thr Lys Leu Val Glu Arg Trp
210                 215                 220 atc tcc gtg tcc ggc gtc gcg gac gac cca aac aac tac ctc ttc tgc     720
Ile Ser Val Ser Gly Val Ala Asp Asp Pro Asn Asn Tyr Leu Phe Cys
225                 230                 235                 240 cgc gtc cgc aag aac ggg gtg gct gcc cct agc gcc acc agc caa ctc     768
Arg Val Arg Lys Asn Gly Val Ala Ala Pro Ser Ala Thr Ser Gln Leu
                245                 250                 255 agc acg agg gcc ttg gaa ggt att ttc gag gcc acc cac cgc ctg atc     816
Ser Thr Arg Ala Leu Glu Gly Ile Phe Glu Ala Thr His Arg Leu Ile
            260                 265                 270 tac ggc gcg aag gat gac agc ggt caa cgc tac ctc gca tgg tcc ggg     864
Tyr Gly Ala Lys Asp Asp Ser Gly Gln Arg Tyr Leu Ala Trp Ser Gly
        275                 280                 285 cac tcc gcc cgc gtt gga gct gct agg gac atg gcc cgc gcc ggt gtt     912
His Ser Ala Arg Val Gly Ala Ala Arg Asp Met Ala Arg Ala Gly Val
        290                 295                 300
```

```
tcc atc ccc gaa atc atg cag gcg ggt gga tgg acg aac gtg aac att    960
Ser Ile Pro Glu Ile Met Gln Ala Gly Gly Trp Thr Asn Val Asn Ile
305             310                 315                 320 gtc atg aac tac att cgc aac ctt gac agc gag acg ggc gca atg gtt   1008
Val Met Asn Tyr Ile Arg Asn Leu Asp Ser Glu Thr Gly Ala Met Val
            325                 330                 335 cgc ctc ctg gaa gat ggc gat ggt ggc agc ggt ggc ggc tcc ggc       1056
Arg Leu Leu Glu Asp Gly Asp Gly Gly Ser Gly Gly Gly Ser Gly
        340                 345                 350 ggt ggc tcg gat cca aca atg ccc cag ttc gac atc ctc tgc aag acc   1104
Gly Gly Ser Asp Pro Thr Met Pro Gln Phe Asp Ile Leu Cys Lys Thr
            355                 360                 365 ccc ccc aag gtg ctc gtg agg cag ttc gtg gag agg ttc gag agg ccc   1152
Pro Pro Lys Val Leu Val Arg Gln Phe Val Glu Arg Phe Glu Arg Pro
370                 375                 380 tcc ggc gag aag atc gcc ctc tgc gcc gcc gag ctc acc tac ctc tgc   1200
Ser Gly Glu Lys Ile Ala Leu Cys Ala Ala Glu Leu Thr Tyr Leu Cys
385                 390                 395                 400 tgg atg atc acc cac aac ggc acc gcc att aag agg gcc acc ttc atg   1248
Trp Met Ile Thr His Asn Gly Thr Ala Ile Lys Arg Ala Thr Phe Met
            405                 410                 415 tca tac aac acc atc atc tcc aac tcc ctc tcc ttc gac atc gtg aac   1296
Ser Tyr Asn Thr Ile Ile Ser Asn Ser Leu Ser Phe Asp Ile Val Asn
            420                 425                 430 aag tcc ctc cag ttc aaa tac aag acc cag aag gcc acc atc ctc gag   1344
Lys Ser Leu Gln Phe Lys Tyr Lys Thr Gln Lys Ala Thr Ile Leu Glu
            435                 440                 445 gcc tcc ctc aag aag ctc atc ccc gcc tgg gag ttc acc atc atc ccc   1392
Ala Ser Leu Lys Lys Leu Ile Pro Ala Trp Glu Phe Thr Ile Ile Pro
450                 455                 460 tac tac ggc cag aag cac cag tcc gac atc acc gac atc gtg tca tcc   1440
Tyr Tyr Gly Gln Lys His Gln Ser Asp Ile Thr Asp Ile Val Ser Ser
465                 470                 475                 480 ctc cag ctt cag ttc gag tcc tcc gag gag gct gac aag ggc aac tcc   1488
Leu Gln Leu Gln Phe Glu Ser Ser Glu Glu Ala Asp Lys Gly Asn Ser
            485                 490                 495 cac tcc aag aag atg ctg aag gcc ctc ctc tcc gag ggc gag tcc atc   1536
His Ser Lys Lys Met Leu Lys Ala Leu Leu Ser Glu Gly Glu Ser Ile
            500                 505                 510 tgg gag atc acc gag aag atc ctc aac tcc ttc gag tac acc tcc agg   1584
Trp Glu Ile Thr Glu Lys Ile Leu Asn Ser Phe Glu Tyr Thr Ser Arg
            515                 520                 525 ttc act aag acc aag acc ctc tac cag ttc ctc ttc ctc gcc acc ttc   1632
Phe Thr Lys Thr Lys Thr Leu Tyr Gln Phe Leu Phe Leu Ala Thr Phe
            530                 535                 540 atc aac tgc ggc agg ttc tca gac atc aag aac gtg gac ccc aag tcc   1680
Ile Asn Cys Gly Arg Phe Ser Asp Ile Lys Asn Val Asp Pro Lys Ser
545                 550                 555                 560 ttc aag ctc gtg cag aac aag tac ctc ggc gtg atc atc cag tgc ctc   1728
Phe Lys Leu Val Gln Asn Lys Tyr Leu Gly Val Ile Ile Gln Cys Leu
            565                 570                 575 gtg acc gag acc aag acc tcc gtg tcc agg cac atc tac ttc ttc tcc   1776
Val Thr Glu Thr Lys Thr Ser Val Ser Arg His Ile Tyr Phe Phe Ser
            580                 585                 590 gct cgc ggc agg atc gac ccc ctc gtg tac ctc gac gag ttc ctc agg   1824
Ala Arg Gly Arg Ile Asp Pro Leu Val Tyr Leu Asp Glu Phe Leu Arg
            595                 600                 605 aac tca gag ccc gtg ctc aag agg gtg aac agg acc ggc aac tcc tcc   1872
Asn Ser Glu Pro Val Leu Lys Arg Val Asn Arg Thr Gly Asn Ser Ser
            610                 615                 620
```

```
tcc aac aag cag gag tac cag ctc ctc aag gac aac ctc gtg agg tcc    1920
Ser Asn Lys Gln Glu Tyr Gln Leu Leu Lys Asp Asn Leu Val Arg Ser
625                 630                 635                 640 tac aac aag gcc ctc aag aag aac gcc ccc tac tcc atc ttc gcc atc    1968
Tyr Asn Lys Ala Leu Lys Lys Asn Ala Pro Tyr Ser Ile Phe Ala Ile
                645                 650                 655 aag aac ggc ccc aag tcc cac atc ggt agg cac ctc atg acc tcc ttc    2016
Lys Asn Gly Pro Lys Ser His Ile Gly Arg His Leu Met Thr Ser Phe
            660                 665                 670 ctc tca atg aag ggc ctc acc gag ctc acc aac gtg gtg ggc aac tgg    2064
Leu Ser Met Lys Gly Leu Thr Glu Leu Thr Asn Val Val Gly Asn Trp
        675                 680                 685 tcc gac aag agg gcc tcc gcc gtg gcc agg acc acc tac acc cac cag    2112
Ser Asp Lys Arg Ala Ser Ala Val Ala Arg Thr Thr Tyr Thr His Gln
    690                 695                 700 atc acc gcc atc ccc gac cac tac ttc gcc ctc gtg tca agg tac tac    2160
Ile Thr Ala Ile Pro Asp His Tyr Phe Ala Leu Val Ser Arg Tyr Tyr
705                 710                 715                 720 gcc tac gac ccc atc tcc aag gag atg atc gcc ctc aag gac gag act    2208
Ala Tyr Asp Pro Ile Ser Lys Glu Met Ile Ala Leu Lys Asp Glu Thr
                725                 730                 735 aac ccc atc gag gag tgg cag cac atc gag cag ctc aag ggc tcc gcc    2256
Asn Pro Ile Glu Glu Trp Gln His Ile Glu Gln Leu Lys Gly Ser Ala
            740                 745                 750 gag ggc tcc atc agg tac ccc gcc tgg aac ggc atc atc tcc cag gag    2304
Glu Gly Ser Ile Arg Tyr Pro Ala Trp Asn Gly Ile Ile Ser Gln Glu
        755                 760                 765 gtg ctc gac tac ctc tcc tcc tac atc aac agg agg atc tga            2346
Val Leu Asp Tyr Leu Ser Ser Tyr Ile Asn Arg Arg Ile
    770                 775                 780

<210> SEQ ID NO 6
<211> LENGTH: 781
<212> TYPE: PRT
<213> ORGANISM: Artificial Sequence
<220> FEATURE:
<223> OTHER INFORMATION: Description of Artificial Sequence: sequence

<400> SEQUENCE: 6

Met Ser Asn Leu Leu Thr Val His Gln Asn Leu Pro Ala Leu Pro Val
 1               5                  10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
```

```
145                 150                 155                 160
Leu Ala Phe Leu Gly Ile Ala Tyr Asn Thr Leu Leu Arg Ile Ala Glu
                165                 170                 175
Ile Ala Arg Ile Arg Val Lys Asp Ile Ser Arg Thr Asp Gly Gly Arg
            180                 185                 190
Met Leu Ile His Ile Gly Arg Thr Lys Thr Leu Val Ser Thr Ala Gly
            195                 200                 205
Val Glu Lys Ala Leu Ser Leu Gly Val Thr Lys Leu Val Glu Arg Trp
    210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
            245                 250                 255
Ser Thr Arg Ala Leu Glu Gly Ile Phe Glu Ala Thr His Arg Leu Ile
            260                 265                 270
Tyr Gly Ala Lys Asp Asp Ser Gly Gln Arg Tyr Leu Ala Trp Ser Gly
        275                 280                 285
His Ser Ala Arg Val Gly Ala Ala Arg Asp Met Ala Arg Ala Gly Val
    290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
            325                 330                 335
Arg Leu Leu Glu Asp Gly Asp Gly Gly Ser Gly Gly Gly Ser Gly
            340                 345                 350
Gly Gly Ser Asp Pro Thr Met Pro Gln Phe Asp Ile Leu Cys Lys Thr
        355                 360                 365
Pro Pro Lys Val Leu Val Arg Gln Phe Val Glu Arg Phe Glu Arg Pro
    370                 375                 380
Ser Gly Glu Lys Ile Ala Leu Cys Ala Ala Glu Leu Thr Tyr Leu Cys
385                 390                 395                 400
Trp Met Ile Thr His Asn Gly Thr Ala Ile Lys Arg Ala Thr Phe Met
            405                 410                 415
Ser Tyr Asn Thr Ile Ile Ser Asn Ser Leu Ser Phe Asp Ile Val Asn
            420                 425                 430
Lys Ser Leu Gln Phe Lys Tyr Lys Thr Gln Lys Ala Thr Ile Leu Glu
        435                 440                 445
Ala Ser Leu Lys Lys Leu Ile Pro Ala Trp Glu Phe Thr Ile Ile Pro
    450                 455                 460
Tyr Tyr Gly Gln Lys His Gln Ser Asp Ile Thr Asp Ile Val Ser Ser
465                 470                 475                 480
Leu Gln Leu Gln Phe Glu Ser Ser Glu Glu Ala Asp Lys Gly Asn Ser
            485                 490                 495
His Ser Lys Lys Met Leu Lys Ala Leu Leu Ser Glu Gly Glu Ser Ile
            500                 505                 510
Trp Glu Ile Thr Glu Lys Ile Leu Asn Ser Phe Glu Tyr Thr Ser Arg
        515                 520                 525
Phe Thr Lys Thr Lys Thr Leu Tyr Gln Phe Leu Phe Leu Ala Thr Phe
    530                 535                 540
Ile Asn Cys Gly Arg Phe Ser Asp Ile Lys Asn Val Asp Pro Lys Ser
545                 550                 555                 560
Phe Lys Leu Val Gln Asn Lys Tyr Leu Gly Val Ile Ile Gln Cys Leu
            565                 570                 575
```

```
Val Thr Glu Thr Lys Thr Ser Val Ser Arg His Ile Tyr Phe Ser
            580                 585                 590

Ala Arg Gly Arg Ile Asp Pro Leu Val Tyr Leu Asp Glu Phe Leu Arg
        595                 600                 605

Asn Ser Glu Pro Val Leu Lys Arg Val Asn Arg Thr Gly Asn Ser Ser
        610                 615                 620

Ser Asn Lys Gln Glu Tyr Gln Leu Leu Lys Asp Asn Leu Val Arg Ser
625                 630                 635                 640

Tyr Asn Lys Ala Leu Lys Lys Asn Ala Pro Tyr Ser Ile Phe Ala Ile
                645                 650                 655

Lys Asn Gly Pro Lys Ser His Ile Gly Arg His Leu Met Thr Ser Phe
            660                 665                 670

Leu Ser Met Lys Gly Leu Thr Glu Leu Thr Asn Val Val Gly Asn Trp
        675                 680                 685

Ser Asp Lys Arg Ala Ser Ala Val Ala Arg Thr Thr Tyr Thr His Gln
        690                 695                 700

Ile Thr Ala Ile Pro Asp His Tyr Phe Ala Leu Val Ser Arg Tyr Tyr
705                 710                 715                 720

Ala Tyr Asp Pro Ile Ser Lys Glu Met Ile Ala Leu Lys Asp Glu Thr
                725                 730                 735

Asn Pro Ile Glu Glu Trp Gln His Ile Glu Gln Leu Lys Gly Ser Ala
            740                 745                 750

Glu Gly Ser Ile Arg Tyr Pro Ala Trp Asn Gly Ile Ile Ser Gln Glu
        755                 760                 765

Val Leu Asp Tyr Leu Ser Ser Tyr Ile Asn Arg Arg Ile
        770                 775                 780

<210> SEQ ID NO 7
<211> LENGTH: 2346
<212> TYPE: DNA
<213> ORGANISM: Artificial Sequence
<220> FEATURE:
<223> OTHER INFORMATION: Description of Artificial Sequence: sequence
      encoding a Cre:FLP polypeptide , Cre from
      Bacteriophage P1 and FLP from Saccharomyces

<400> SEQUENCE: 7
atggccaatt tactgaccgt acaccaaaat ttgcctgcat taccggtcga tgcaacgagt      60
gatgaggttc gcaagaacct gatggacatg ttcagggatc gccaggcgtt ttctgagcat     120
acctggaaaa tgcttctgtc cgtttgccgg tcgtgggcgg catggtgcaa gttgaataac     180
cggaaatggt tcccgcagaa acctgaagat gttcgcgatt atcttctata tcttcaggcg     240
cgcggtctgg cagtaaaaac tatccagcaa catttgggcc agctaaacat gcttcatcgt     300
cggtccgggc tgccacgacc aagtgacagc aatgctgttt cactggttat gcggcggatc     360
cgaaaagaaa acgttgatgc cggtgaacgt gcaaacagg ctctagcgtt cgaacgcact     420
gatttcgacc aggttcgttc actcatggaa aatagcgatc gctgccagga tacgtaat     480 ctggcatttc tggggattgc ttataacacc ctgttacgta tagccgaaat tgccaggatc     540
agggttaaag atatctcacg tactgacggt gggagaatgt taatccatat ggcagaacg      600 aaaacgctgg ttagcaccgc aggtgtagag aaggcactta gcctgggggt aactaaactg     660
gtcgagcgat ggatttccgt ctctggtgta gctgatgatc cgaataacta cctgttttgc     720
cgggtcagaa aaatggtgt tgccgcgcca tctgccacca gccagctatc aactcgcgcc     780
ctggaaggga ttttttgaagc aactcatcga ttgatttacg gcgctaagga tgactctggt     840
```

```
cagagatacc tggcctggtc tggacacagt gcccgtgtcg agccgcgcg  agatatggcc    900 cgcgctggag tttcaatacc ggagatcatg caagctggtg ctggaccaa  tgtaaatatt    960 gtcatgaact atatccgtaa cctggatagt gaaacagggg caatggtgcg cctgctggaa   1020
gatggcgatg gtggcggcag cggtggcggc tccggcggtg gctcggatcc aacaatgcca   1080
caatttgata tattatgtaa acaccacct aaggtgcttg ttcgtcagtt tgtggaaagg    1140
tttgagagac cttccggaga gaaaatagca ttatgtgctg ctgaactaac ctatttatgt   1200
tggatgatta cacataacgg aacagcaatc aagagagcca cattcatgag ctataatact   1260
atcataagca attcgctgag tttggatatc gtcaacaagt cactgcagtt taaatacaag   1320
acgcaaaaag caacaattct ggaagcctca ttaaagaaat tgattcctgc ttgggaattt   1380
acaattattc cttactatgg acaaaaacat caatctgata tcactgatat tgtaagtagt   1440
ttgcaattac agttcgaatc atcggaagaa gcagataagg gaaatagcca cagtaaaaaa   1500
atgcttaaag cacttctaag tgagggtgaa agcatctggg agatcactga gaaaatacta   1560
aattcgtttg agtatacttc gagatttaca aaaacaaaaa ctttataccaa ttcctcttc    1620 ctagctactt tcatcaattg tggaagattc agcgatatta agaacgttga tccgaaatca   1680
tttaaattag tccaaaataa gtatctggga gtaataatcc agtgtttagt gacagagaca   1740
aagacaagcg ttagtaggca catatacttc tttagcgcaa ggggtaggat cgatccactt   1800
gtatatttgg atgaattttt gaggaattct gaaccagtcc taaaacgagt aaataggacc   1860
ggcaattctt caagcaacaa gcaggaatac caattattaa aagataactt agtcagatcg   1920
tacaacaaag ctttgaagaa aaatgcgcct tattcaatct tgctataaa aaatggccca    1980 aaatctcaca ttggaagaca tttgatgacc tcatttcttt caatgaaggg cctaacggag   2040
ttgactaatg ttgtgggaaa ttggagcgat aagcgtgctt ctgccgtggc caggacaacg   2100
tatactcatc agataacagc aatacctgat cactacttcg cactagtttc tcggtactat   2160
gcatatgatc caatatcaaa ggaaatgata gcattgaagg atgagactaa tccaattgag   2220
gagtggcagc atatagaaca gctaaagggt agtgctgaag gaagcatacg atacccccgca   2280 tggaatggga taatatcaca ggaggtacta gactaccttt catcctacat aaatagacgc   2340
atataa                                                              2346
```

<210> SEQ ID NO 8
<211> LENGTH: 2346
<212> TYPE: DNA
<213> ORGANISM: Artificial Sequence
<220> FEATURE:
<223> OTHER INFORMATION: Description of Artificial Sequence: Sequence
      encoding a FLPm:Cre polypeptide, FLP from
      Saccharomyces (maize preferred codons), and Cre
      from Bacteriophage P1
<220> FEATURE:
<221> NAME/KEY: CDS
<222> LOCATION: (1)..(2346)

<400> SEQUENCE: 8

```
atg ccc cag ttc gac atc ctc tgc aag acc ccc ccc aag gtg ctc gtg      48
Met Pro Gln Phe Asp Ile Leu Cys Lys Thr Pro Pro Lys Val Leu Val
 1               5                  10                  15 agg cag ttc gtg gag agg ttc gag agg ccc tcc ggc gag aag atc gcc      96
Arg Gln Phe Val Glu Arg Phe Glu Arg Pro Ser Gly Glu Lys Ile Ala
            20                  25                  30 ctc tgc gcc gcc gag ctc acc tac ctc tgc tgg atg atc acc cac aac     144
Leu Cys Ala Ala Glu Leu Thr Tyr Leu Cys Trp Met Ile Thr His Asn
```

```
                35                  40                  45
ggc acc gcc att aag agg gcc acc ttc atg tca tac aac acc atc atc        192
Gly Thr Ala Ile Lys Arg Ala Thr Phe Met Ser Tyr Asn Thr Ile Ile
     50                  55                  60 tcc aac tcc ctc tcc ttc gac atc gtg aac aag tcc ctc cag ttc aaa        240
Ser Asn Ser Leu Ser Phe Asp Ile Val Asn Lys Ser Leu Gln Phe Lys
 65                  70                  75                  80 tac aag acc cag aag gcc acc atc ctc gag gcc tcc ctc aag aag ctc        288
Tyr Lys Thr Gln Lys Ala Thr Ile Leu Glu Ala Ser Leu Lys Lys Leu
             85                  90                  95 atc ccc gcc tgg gag ttc acc atc atc ccc tac tac ggc cag aag cac        336
Ile Pro Ala Trp Glu Phe Thr Ile Ile Pro Tyr Tyr Gly Gln Lys His
                100                 105                 110 cag tcc gac atc acc gac atc gtg tca tcc ctc cag ctt cag ttc gag        384
Gln Ser Asp Ile Thr Asp Ile Val Ser Ser Leu Gln Leu Gln Phe Glu
            115                 120                 125 tcc tcc gag gag gct gac aag ggc aac tcc cac tcc aag aag atg ctg        432
Ser Ser Glu Glu Ala Asp Lys Gly Asn Ser His Ser Lys Lys Met Leu
        130                 135                 140 aag gcc ctc ctc tcc gag ggc gag tcc atc tgg gag atc acc gag aag        480
Lys Ala Leu Leu Ser Glu Gly Glu Ser Ile Trp Glu Ile Thr Glu Lys
145                 150                 155                 160 atc ctc aac tcc ttc gag tac acc tcc agg ttc act aag acc aag acc        528
Ile Leu Asn Ser Phe Glu Tyr Thr Ser Arg Phe Thr Lys Thr Lys Thr
                165                 170                 175 ctc tac cag ttc ctc ttc ctc gcc acc ttc atc aac tgc ggc agg ttc        576
Leu Tyr Gln Phe Leu Phe Leu Ala Thr Phe Ile Asn Cys Gly Arg Phe
            180                 185                 190 tca gac atc aag aac gtg gac ccc aag tcc ttc aag ctc gtg cag aac        624
Ser Asp Ile Lys Asn Val Asp Pro Lys Ser Phe Lys Leu Val Gln Asn
        195                 200                 205 aag tac ctc ggc gtg atc atc cag tgc ctc gtg acc gag acc aag acc        672
Lys Tyr Leu Gly Val Ile Ile Gln Cys Leu Val Thr Glu Thr Lys Thr
    210                 215                 220 tcc gtg tcc agg cac atc tac ttc ttc tcc gct cgc ggc agg atc gac        720
Ser Val Ser Arg His Ile Tyr Phe Phe Ser Ala Arg Gly Arg Ile Asp
225                 230                 235                 240 ccc ctc gtg tac ctc gac gag ttc ctc agg aac tca gag ccc gtg ctc        768
Pro Leu Val Tyr Leu Asp Glu Phe Leu Arg Asn Ser Glu Pro Val Leu
                245                 250                 255 aag agg gtg aac agg acc ggc aac tcc tcc tcc aac aag cag gag tac        816
Lys Arg Val Asn Arg Thr Gly Asn Ser Ser Ser Asn Lys Gln Glu Tyr
            260                 265                 270 cag ctc ctc aag gac aac ctc gtg agg tcc tac aac aag gcc ctc aag        864
Gln Leu Leu Lys Asp Asn Leu Val Arg Ser Tyr Asn Lys Ala Leu Lys
        275                 280                 285 aag aac gcc ccc tac tcc atc ttc gcc atc aag aac ggc ccc aag tcc        912
Lys Asn Ala Pro Tyr Ser Ile Phe Ala Ile Lys Asn Gly Pro Lys Ser
    290                 295                 300 cac atc ggt agg cac ctc atg acc tcc ttc ctc tca atg aag ggc ctc        960
His Ile Gly Arg His Leu Met Thr Ser Phe Leu Ser Met Lys Gly Leu
305                 310                 315                 320 acc gag ctc acc aac gtg gtg ggc aac tgg tcc gac aag agg gcc tcc       1008
Thr Glu Leu Thr Asn Val Val Gly Asn Trp Ser Asp Lys Arg Ala Ser
                325                 330                 335 gcc gtg gcc agg acc acc tac acc cac cag atc acc gcc atc ccc gac       1056
Ala Val Ala Arg Thr Thr Tyr Thr His Gln Ile Thr Ala Ile Pro Asp
            340                 345                 350 cac tac ttc gcc ctc gtg tca agg tac tac gcc tac gac ccc atc tcc       1104
```

```
                    His Tyr Phe Ala Leu Val Ser Arg Tyr Tyr Ala Tyr Asp Pro Ile Ser
                                355                 360                 365 aag gag atg atc gcc ctc aag gac gag act aac ccc atc gag gag tgg      1152
Lys Glu Met Ile Ala Leu Lys Asp Glu Thr Asn Pro Ile Glu Glu Trp
            370                 375                 380 cag cac atc gag cag ctc aag ggc tcc gcc gag ggc tcc atc agg tac      1200
Gln His Ile Glu Gln Leu Lys Gly Ser Ala Glu Gly Ser Ile Arg Tyr
385                 390                 395                 400 ccc gcc tgg aac ggc atc atc tcc cag gag gtg ctc gac tac ctc tcc      1248
Pro Ala Trp Asn Gly Ile Ile Ser Gln Glu Val Leu Asp Tyr Leu Ser
                405                 410                 415 tcc tac atc aac agg agg atc ggt ggc ggc agc ggt ggc ggc tcc ggc      1296
Ser Tyr Ile Asn Arg Arg Ile Gly Gly Gly Ser Gly Gly Gly Ser Gly
            420                 425                 430 ggt ggc tcg gat cca acc atg gcc aat tta ctg acc gta cac caa aat      1344
Gly Gly Ser Asp Pro Thr Met Ala Asn Leu Leu Thr Val His Gln Asn
                435                 440                 445 ttg cct gca tta ccg gtc gat gca acg agt gat gag gtt cgc aag aac      1392
Leu Pro Ala Leu Pro Val Asp Ala Thr Ser Asp Glu Val Arg Lys Asn
            450                 455                 460 ctg atg gac atg ttc agg gat cgc cag gcg ttt tct gag cat acc tgg      1440
Leu Met Asp Met Phe Arg Asp Arg Gln Ala Phe Ser Glu His Thr Trp
465                 470                 475                 480 aaa atg ctt ctg tcc gtt tgc cgg tcg tgg gcg gca tgg tgc aag ttg      1488
Lys Met Leu Leu Ser Val Cys Arg Ser Trp Ala Ala Trp Cys Lys Leu
                485                 490                 495 aat aac cgg aaa tgg ttt ccc gca gaa cct gaa gat gtt cgc gat tat      1536
Asn Asn Arg Lys Trp Phe Pro Ala Glu Pro Glu Asp Val Arg Asp Tyr
            500                 505                 510 ctt cta tat ctt cag gcg cgc ggt ctg gca gta aaa act atc cag caa      1584
Leu Leu Tyr Leu Gln Ala Arg Gly Leu Ala Val Lys Thr Ile Gln Gln
            515                 520                 525 cat ttg ggc cag cta aac atg ctt cat cgt cgg tcc ggg ctg cca cga      1632
His Leu Gly Gln Leu Asn Met Leu His Arg Arg Ser Gly Leu Pro Arg
            530                 535                 540 cca agt gac agc aat gct gtt tca ctg gtt atg cgg cgg atc cga aaa      1680
Pro Ser Asp Ser Asn Ala Val Ser Leu Val Met Arg Arg Ile Arg Lys
545                 550                 555                 560 gaa aac gtt gat gcc ggt gaa cgt gca aaa cag gct cta gcg ttc gaa      1728
Glu Asn Val Asp Ala Gly Glu Arg Ala Lys Gln Ala Leu Ala Phe Glu
                565                 570                 575 cgc act gat ttc gac cag gtt cgt tca ctc atg gaa aat agc gat cgc      1776
Arg Thr Asp Phe Asp Gln Val Arg Ser Leu Met Glu Asn Ser Asp Arg
            580                 585                 590 tgc cag gat ata cgt aat ctg gca ttt ctg ggg att gct tat aac acc      1824
Cys Gln Asp Ile Arg Asn Leu Ala Phe Leu Gly Ile Ala Tyr Asn Thr
            595                 600                 605 ctg tta cgt ata gcc gaa att gcc agg atc agg gtt aaa gat atc tca      1872
Leu Leu Arg Ile Ala Glu Ile Ala Arg Ile Arg Val Lys Asp Ile Ser
610                 615                 620 cgt act gac ggt ggg aga atg tta atc cat att ggc aga acg aaa acg      1920
Arg Thr Asp Gly Gly Arg Met Leu Ile His Ile Gly Arg Thr Lys Thr
            625                 630                 635                 640 ctg gtt agc acc gca ggt gta gag aag gca ctt agc ctg ggg gta act      1968
Leu Val Ser Thr Ala Gly Val Glu Lys Ala Leu Ser Leu Gly Val Thr
                645                 650                 655 aaa ctg gtc gag cga tgg att tcc gtc tct ggt gta gct gat gat ccg      2016
Lys Leu Val Glu Arg Trp Ile Ser Val Ser Gly Val Ala Asp Asp Pro
            660                 665                 670
```

-continued

```
aat aac tac ctg ttt tgc cgg gtc aga aaa aat ggt gtt gcc gcg cca      2064
Asn Asn Tyr Leu Phe Cys Arg Val Arg Lys Asn Gly Val Ala Ala Pro
        675                 680                 685 tct gcc acc agc cag cta tca act cgc gcc ctg gaa ggg att ttt gaa      2112
Ser Ala Thr Ser Gln Leu Ser Thr Arg Ala Leu Glu Gly Ile Phe Glu
    690                 695                 700 gca act cat cga ttg att tac ggc gct aag gat gac tct ggt cag aga      2160
Ala Thr His Arg Leu Ile Tyr Gly Ala Lys Asp Asp Ser Gly Gln Arg
705                 710                 715                 720 tac ctg gcc tgg tct gga cac agt gcc cgt gtc gga gcc gcg cga gat      2208
Tyr Leu Ala Trp Ser Gly His Ser Ala Arg Val Gly Ala Ala Arg Asp
                725                 730                 735 atg gcc cgc gct gga gtt tca ata ccg gag atc atg caa gct ggt ggc      2256
Met Ala Arg Ala Gly Val Ser Ile Pro Glu Ile Met Gln Ala Gly Gly
            740                 745                 750 tgg acc aat gta aat att gtc atg aac tat atc cgt aac ctg gat agt      2304
Trp Thr Asn Val Asn Ile Val Met Asn Tyr Ile Arg Asn Leu Asp Ser
        755                 760                 765 gaa aca ggg gca atg gtg cgc ctg ctg gaa gat ggc gat tag              2346
Glu Thr Gly Ala Met Val Arg Leu Leu Glu Asp Gly Asp
    770                 775                 780
```

<210> SEQ ID NO 9
<211> LENGTH: 781
<212> TYPE: PRT
<213> ORGANISM: Artificial Sequence
<220> FEATURE:
<223> OTHER INFORMATION: Description of Artificial Sequence: Sequence

<400> SEQUENCE: 9

```
Met Pro Gln Phe Asp Ile Leu Cys Lys Thr Pro Pro Lys Val Leu Val
  1               5                  10                  15

Arg Gln Phe Val Glu Arg Phe Glu Arg Pro Ser Gly Glu Lys Ile Ala
             20                  25                  30

Leu Cys Ala Ala Glu Leu Thr Tyr Leu Cys Trp Met Ile Thr His Asn
         35                  40                  45

Gly Thr Ala Ile Lys Arg Ala Thr Phe Met Ser Tyr Asn Thr Ile Ile
     50                  55                  60

Ser Asn Ser Leu Ser Phe Asp Ile Val Asn Lys Ser Leu Gln Phe Lys
 65                  70                  75                  80

Tyr Lys Thr Gln Lys Ala Thr Ile Leu Glu Ala Ser Leu Lys Lys Leu
                 85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220
```

-continued

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
            245                 250                 255

Lys Arg Val Asn Arg Thr Gly Asn Ser Ser Asn Lys Gln Glu Tyr
        260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
            325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
        370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile Gly Gly Gly Ser Gly Gly Gly Ser Gly
            420                 425                 430

Gly Gly Ser Asp Pro Thr Met Ala Asn Leu Leu Thr Val His Gln Asn
        435                 440                 445

Leu Pro Ala Leu Pro Val Asp Ala Thr Ser Asp Glu Val Arg Lys Asn
        450                 455                 460

Leu Met Asp Met Phe Arg Asp Arg Gln Ala Phe Ser Glu His Thr Trp
465                 470                 475                 480

Lys Met Leu Leu Ser Val Cys Arg Ser Trp Ala Ala Trp Cys Lys Leu
                485                 490                 495

Asn Asn Arg Lys Trp Phe Pro Ala Glu Pro Glu Asp Val Arg Asp Tyr
            500                 505                 510

Leu Leu Tyr Leu Gln Ala Arg Gly Leu Ala Val Lys Thr Ile Gln Gln
        515                 520                 525

His Leu Gly Gln Leu Asn Met Leu His Arg Arg Ser Gly Leu Pro Arg
530                 535                 540

Pro Ser Asp Ser Asn Ala Val Ser Leu Val Met Arg Arg Ile Arg Lys
545                 550                 555                 560

Glu Asn Val Asp Ala Gly Glu Arg Ala Lys Gln Ala Leu Ala Phe Glu
                565                 570                 575

Arg Thr Asp Phe Asp Gln Val Arg Ser Leu Met Glu Asn Ser Asp Arg
            580                 585                 590

Cys Gln Asp Ile Arg Asn Leu Ala Phe Leu Gly Ile Ala Tyr Asn Thr
        595                 600                 605

Leu Leu Arg Ile Ala Glu Ile Ala Arg Ile Arg Val Lys Asp Ile Ser
        610                 615                 620

Arg Thr Asp Gly Gly Arg Met Leu Ile His Ile Gly Arg Thr Lys Thr
625                 630                 635                 640

-continued

```
Leu Val Ser Thr Ala Gly Val Glu Lys Ala Leu Ser Leu Gly Val Thr
                645                 650                 655
Lys Leu Val Glu Arg Trp Ile Ser Val Ser Gly Val Ala Asp Asp Pro
            660                 665                 670
Asn Asn Tyr Leu Phe Cys Arg Val Arg Lys Asn Gly Val Ala Ala Pro
        675                 680                 685
Ser Ala Thr Ser Gln Leu Ser Thr Arg Ala Leu Glu Gly Ile Phe Glu
    690                 695                 700
Ala Thr His Arg Leu Ile Tyr Gly Ala Lys Asp Asp Ser Gly Gln Arg
705                 710                 715                 720
Tyr Leu Ala Trp Ser Gly His Ser Ala Arg Val Gly Ala Ala Arg Asp
                725                 730                 735
Met Ala Arg Ala Gly Val Ser Ile Pro Glu Ile Met Gln Ala Gly Gly
            740                 745                 750
Trp Thr Asn Val Asn Ile Val Met Asn Tyr Ile Arg Asn Leu Asp Ser
        755                 760                 765
Glu Thr Gly Ala Met Val Arg Leu Leu Glu Asp Gly Asp
    770                 775                 780

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:  minimal
      wild-type FRT recombination site

<400> SEQUENCE: 10
gaagttccta ttctctagaa agtataggaa cttc                                34

<210> SEQ ID NO 11
<211> LENGTH: 781
<212> TYPE: PRT
<213> ORGANISM: Artificial Sequence
<220> FEATURE:
<223> OTHER INFORMATION: Description of Artificial Sequence: Cre:FLP
      polypeptide, Cre from Bacteriophage P1 and FLP
      from Saccharomyces

<400> SEQUENCE: 11

Met Ala Asn Leu Leu Thr Val His Gln Asn Leu Pro Ala Leu Pro Val
  1               5                  10                  15
Asp Ala Thr Ser Asp Glu Val Arg Lys Asn Leu Met Asp Met Phe Arg
             20                  25                  30
Asp Arg Gln Ala Phe Ser Glu His Thr Trp Lys Met Leu Leu Ser Val
         35                  40                  45
Cys Arg Ser Trp Ala Ala Trp Cys Lys Leu Asn Asn Arg Lys Trp Phe
     50                  55                  60
Pro Ala Glu Pro Glu Asp Val Arg Asp Tyr Leu Leu Tyr Leu Gln Ala
 65                  70                  75                  80
Arg Gly Leu Ala Val Lys Thr Ile Gln Gln His Leu Gly Gln Leu Asn
                 85                  90                  95
Met Leu His Arg Arg Ser Gly Leu Pro Arg Pro Ser Asp Ser Asn Ala
            100                 105                 110
Val Ser Leu Val Met Arg Arg Ile Arg Lys Glu Asn Val Asp Ala Gly
        115                 120                 125
Glu Arg Ala Lys Gln Ala Leu Ala Phe Glu Arg Thr Asp Phe Asp Gln
    130                 135                 140
```

-continued

```
Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp Gly Gly Ser Gly Gly Gly Ser Gly
            340                 345                 350

Gly Gly Ser Asp Pro Thr Met Pro Gln Phe Asp Ile Leu Cys Lys Thr
        355                 360                 365

Pro Pro Lys Val Leu Val Arg Gln Phe Val Glu Arg Phe Glu Arg Pro
    370                 375                 380

Ser Gly Glu Lys Ile Ala Leu Cys Ala Ala Glu Leu Thr Tyr Leu Cys
385                 390                 395                 400

Trp Met Ile Thr His Asn Gly Thr Ala Ile Lys Arg Ala Thr Phe Met
                405                 410                 415

Ser Tyr Asn Thr Ile Ile Ser Asn Ser Leu Ser Leu Asp Ile Val Asn
            420                 425                 430

Lys Ser Leu Gln Phe Lys Tyr Lys Thr Gln Lys Ala Thr Ile Leu Glu
        435                 440                 445

Ala Ser Leu Lys Lys Leu Ile Pro Ala Trp Glu Phe Thr Ile Ile Pro
    450                 455                 460

Tyr Tyr Gly Gln Lys His Gln Ser Asp Ile Thr Asp Ile Val Ser Ser
465                 470                 475                 480

Leu Gln Leu Gln Phe Glu Ser Ser Glu Glu Ala Asp Lys Gly Asn Ser
                485                 490                 495

His Ser Lys Lys Met Leu Lys Ala Leu Leu Ser Glu Gly Glu Ser Ile
            500                 505                 510

Trp Glu Ile Thr Glu Lys Ile Leu Asn Ser Phe Glu Tyr Thr Ser Arg
        515                 520                 525

Phe Thr Lys Thr Lys Thr Leu Tyr Gln Phe Leu Phe Leu Ala Thr Phe
    530                 535                 540

Ile Asn Cys Gly Arg Phe Ser Asp Ile Lys Asn Val Asp Pro Lys Ser
545                 550                 555                 560

Phe Lys Leu Val Gln Asn Lys Tyr Leu Gly Val Ile Ile Gln Cys Leu
```

-continued

```
                    565                 570                 575
Val Thr Glu Thr Lys Thr Ser Val Ser Arg His Ile Tyr Phe Phe Ser
            580                 585                 590

Ala Arg Gly Arg Ile Asp Pro Leu Val Tyr Leu Asp Glu Phe Leu Arg
            595                 600                 605

Asn Ser Glu Pro Val Leu Lys Arg Val Asn Arg Thr Gly Asn Ser Ser
            610                 615                 620

Ser Asn Lys Gln Glu Tyr Gln Leu Leu Lys Asp Asn Leu Val Arg Ser
625                 630                 635                 640

Tyr Asn Lys Ala Leu Lys Lys Asn Ala Pro Tyr Ser Ile Phe Ala Ile
                645                 650                 655

Lys Asn Gly Pro Lys Ser His Ile Gly Arg His Leu Met Thr Ser Phe
                660                 665                 670

Leu Ser Met Lys Gly Leu Thr Glu Leu Thr Asn Val Val Gly Asn Trp
                675                 680                 685

Ser Asp Lys Arg Ala Ser Ala Val Ala Arg Thr Thr Tyr Thr His Gln
        690                 695                 700

Ile Thr Ala Ile Pro Asp His Tyr Phe Ala Leu Val Ser Arg Tyr Tyr
705                 710                 715                 720

Ala Tyr Asp Pro Ile Ser Lys Glu Met Ile Ala Leu Lys Asp Glu Thr
                725                 730                 735

Asn Pro Ile Glu Glu Trp Gln His Ile Glu Gln Leu Lys Gly Ser Ala
                740                 745                 750

Glu Gly Ser Ile Arg Tyr Pro Ala Trp Asn Gly Ile Ile Ser Gln Glu
        755                 760                 765

Val Leu Asp Tyr Leu Ser Ser Tyr Ile Asn Arg Arg Ile
        770                 775                 780
```